United States Patent
Downs et al.

(10) Patent No.: US 11,610,267 B2
(45) Date of Patent: Mar. 21, 2023

(54) SYSTEM AND METHOD FOR RULES-DRIVEN ADJUDICATION

(71) Applicant: Myndshft Technologies, Inc., Dover, DE (US)

(72) Inventors: Brian J. Downs, Scottsdale, AZ (US); Nelson T. Tran, Mesa, AZ (US); Alec D Iverson, Mesa, AZ (US); Bukola A. Robertson, Phoenix, AZ (US); Jorden K. Kreps, Fargo, ND (US); John K. Moore, Phoenix, AZ (US); Tyler Wince, Mesa, AZ (US)

(73) Assignee: Myndshft Technologies, Inc, Mesa, AZ (US)

( * ) Notice: Subject to any disclaimer, the term of this patent is extended or adjusted under 35 U.S.C. 154(b) by 123 days.

(21) Appl. No.: 16/997,863

(22) Filed: Aug. 19, 2020

(65) Prior Publication Data
US 2021/0056637 A1    Feb. 25, 2021

Related U.S. Application Data

(60) Provisional application No. 62/890,369, filed on Aug. 22, 2019.

(51) Int. Cl.
| | |
|---|---|
| *G06Q 40/08* | (2012.01) |
| *G16H 10/60* | (2018.01) |
| *G16H 70/20* | (2018.01) |
| *G06Q 10/10* | (2023.01) |
| *G06N 5/04* | (2023.01) |

(Continued)

(52) U.S. Cl.
CPC .............. *G06Q 40/08* (2013.01); *G06N 5/04* (2013.01); *G06Q 10/10* (2013.01); *G16H 10/60* (2018.01); *G16H 40/20* (2018.01); *G16H 70/20* (2018.01); *G06Q 10/105* (2013.01); *G06Q 50/26* (2013.01)

(58) Field of Classification Search
CPC ........ G16H 70/20; G16H 10/60; G16H 40/20; G06Q 50/26; G06Q 40/08; G06Q 10/10; G06Q 10/105; G06N 20/00; G06N 5/04
See application file for complete search history.

(56) References Cited

U.S. PATENT DOCUMENTS

| | | | |
|---|---|---|---|
| 5,786,816 A | 7/1998 | Macrae et al. | |
| 10,192,260 B2 * | 1/2019 | Tholl | G06Q 40/08 |

(Continued)

FOREIGN PATENT DOCUMENTS

| | | | | |
|---|---|---|---|---|
| CA | 3051044 A1 * | 9/2020 | | G06N 20/00 |

*Primary Examiner* — Scott S Trotter
(74) *Attorney, Agent, or Firm* — Booth Udall Fuller, PLC

(57) ABSTRACT

A system and method for rules-driven adjudication is disclosed. The system includes a storage includes a rule library having a plurality of rules, each rule being in a human-readable format and including a first data tag, a comparator, a comparison value, and a result. The system also includes a rules manager configured to receive and store a new rule. The system includes a rules evaluator configured to receive an adjudication request having a data object associated with a data tag, and evaluate the request and create a primary determination by applying a first rule to the request, and further applying a first subsequent rule and all logically adjacent rules until all logically adjacent rules have been exhausted and the primary determination is an indefinite outcome or the applying of a final rule returns an outcome that becomes the primary determination.

20 Claims, 12 Drawing Sheets

(51) Int. Cl.
*G16H 40/20* (2018.01)
*G06Q 50/26* (2012.01)
*G06Q 10/105* (2023.01)

(56) References Cited

U.S. PATENT DOCUMENTS

2002/0046047 A1 4/2002 Budd
2006/0111933 A1 5/2006 Wheeler

* cited by examiner

SYSTEM AND METHOD FOR RULES-DRIVEN ADJUDICATION

RELATED APPLICATIONS

This application claims the benefit of U.S. provisional patent application 62/890,369, filed Aug. 22, 2019 titled "Rules Engine System For Healthcare Prior Authorization," the entirety of the disclosure of which is hereby incorporated by this reference.

TECHNICAL FIELD

Aspects of this document relate generally to rule-based adjudication systems and methods.

BACKGROUND

The utility of rules and policies, as a concept, is undeniable. From the laws that govern societies to the policies that ensure customer experience that is consistent throughout a nation-wide restaurant chain, the applicability of sets of rules is universal. Across a wide range of industries and endeavors, results have been improved, products have been enhanced, and efficiency increased through the application of rules and policies. The codification and use of a rule set allows for policy to be enforce fairly and with uniformity, even within a large and distributed organization. These rules help provide consistency, granting a predictability that increases overall efficiency. The creation and use of rules and policies allow entities to be more deliberate in their actions, ensuring they are better able to achieve their intended purpose.

However, the definition and application of rules is not without cost. Once defined, rules must be distributed and explained to all who will be charged with their application. Any update to the rules could require retraining an entire workforce before they are consistently applied. Additionally, the conventional method of relying on people to apply the rules, using their interpretation and judgement, introduces the possibility of deviations from the intended result. At best, people can make mistakes or misunderstand a rule; at worst, the application of rules may be tainted by bias that can be hard to prevent, let alone detect. Furthermore, complicated and/or large rule sets, such as the rules for determining prior authorization for a medical procedure, can be slow to apply, and can result in a decision making process that is sometimes opaque to the stakeholders.

SUMMARY

According to an aspect, a system for rules-driven adjudication may comprise a processor communicatively coupled to a memory and a network interface, the network interface communicatively coupled to a network. The system may comprise a storage comprising at least one rule library, each of the at least one rule library comprising a plurality of rules. Each rule of the plurality of rules may be in a human-readable format and comprise a first data tag, a comparator, a comparison value, and a result returned upon satisfaction of the comparator. The comparison value may be one of a second data tag and an external value. The result may be one of an outcome and at least one subsequent rule, each outcome being one of a plurality of potential outcomes comprising at least one definite outcome and at least one indefinite outcome. The system may comprise a rules manager configured to receive a new rule through the network interface from a first client, and store the new rule in one of the at least one rule library. The system may comprise a rules evaluator configured to receive an adjudication request through the network interface from a second client, the adjudication request comprising at least one data object, each of the at least one data object being associated with a different data tag. The rules evaluator may be configured to identify an appropriate rule library from among the at least one rule library to apply based at least on the adjudication request. The rules evaluator may be configured to evaluate the adjudication request and create a primary determination by applying a first rule of the appropriate rule library to the adjudication request, using data objects from the adjudication request indicated by at least one data tag of the first rule, and further applying a first subsequent rule of the at least one subsequent rules and all logically adjacent rules within the appropriate rule library until all logically adjacent rules have been exhausted and the primary determination is an indefinite outcome or the applying of a final rule returns an outcome that becomes the primary determination. The rules evaluator may be configured to send, for primary determinations having an indefinite outcome, an escalated request to the first client communicatively coupled to the rules evaluator, the escalated request comprising at least the adjudication request. The rules evaluator may be configured to receive a secondary determination from the first client, the secondary determination indicating the result of an evaluation of the escalated request performed by a first agent. The rules evaluator may be configured to send an adjudication result to the second client through the network interface in response to one of the primary determination having a definite outcome and the receipt of a secondary determination, the adjudication result comprising one of the primary determination and the secondary determination. The rules evaluator may be configured to create a first probationary rule in response to the receipt of the secondary determination by the rules evaluator, the first probationary rule may function as an exception to a target rule that is the final rule. The first data tag of the first probationary rule may be the same as the first data tag of the target rule, the result of the first probationary rule may be equal to the secondary determination, and at least one of the comparator and the comparison value of the first probationary rule may deviate from what is defined in the target rule to create an exception that, when applied to the adjudication request before the application of the target rule, the result is the same as the secondary determination. The rules evaluator may be configured to store the first probationary rule within the storage, the first probationary rule may further comprise a success rate. The rules evaluator may be configured to add to the target rule a reference pointing to the first probationary rule within the storage. The rules evaluator may be configured to apply the first probationary rule to another adjudication request resulting in the application of the target rule and the sending of another escalated request. The rules evaluator may be configured to compare the secondary determination received in response to the another escalated request with the result of the application of the first probationary rule to the another adjudication request, and update the success rate of the first probationary rule. The rules evaluator may be configured to refine the first probationary rule by one of modifying at least one of the comparator and the comparison value of the first probationary rule and creating a second probationary rule as an exception to the first probationary rule, in response to the first probationary rule's failure to match the secondary determination received in response to the another escalated request. The rules evaluator may be configured to insert the first probationary rule into the appropriate rule library in response to at least one of the receipt of a manual approval and the success rate of the first probationary rule surpassing a predefined threshold. The external value may be obtained outside of the adjudication request.

The system for rules-driven adjudication presented above may further comprise the adjudication request being a request for prior authorization and comprise patient information, policy information, and treatment information comprising a medical code. The first client may be an insurance provider client. The second client may be a healthcare provider client. The at least one definite outcome may comprise an approval, a denial, and an indication that prior authorization is not required. The at least one indefinite outcome may comprise an indication that the system in unable to evaluate the request. The rules manager may be further configured to provide, through the network interface, an interface in which at least one rule library is formatted and through which the at least one rule library is made available to a user as a human readable resource. At least one of the first data tag and the second data tag of at least one rule in the appropriate rule library may be associated with a derived data object missing from the adjudication request and may be defined by an expression comprising one or more operations performed on at least one data object of the adjudication request, and wherein the plurality of rules are stored in a JSON format.

According to another aspect, a system for rules-driven adjudication may comprise a processor communicatively coupled to a memory and a network interface, the network interface communicatively coupled to a network. The system for rules-driven adjudication may comprise a storage comprising at least one rule library. Each of the at least one rule library may comprise a plurality of rules, each rule of the plurality of rules being in a human-readable format and comprising a first data tag, a comparator, a comparison value, and a result returned upon satisfaction of the comparator. The comparison value may be one of a second data tag and an external value and the result may be one of an outcome and at least one subsequent rule. Each outcome may be one of a plurality of potential outcomes comprising at least one definite outcome and at least one indefinite outcome. A rules manager may be configured to receive a new rule through the network interface from a first client, and store the new rule in one of the at least one rule library. A rules evaluator may be configured to receive an adjudication request through the network interface from a second client, the adjudication request comprising at least one data object, each of the at least one data object being associated with a different data tag. The rules evaluator may identify an appropriate rule library from among the at least one rule library to apply based at least on the adjudication request. The rules evaluator may evaluate the adjudication request and create a primary determination by applying a first rule of the appropriate rule library to the adjudication request, using data objects from the adjudication request indicated by at least one data tag of the first rule, and further applying a first subsequent rule of the at least one subsequent rules and all logically adjacent rules within the appropriate rule library until all logically adjacent rules have been exhausted and the primary determination is an indefinite outcome or the applying of a final rule returns an outcome that becomes the primary determination. The rules evaluator may send an adjudication result to the second client through the network interface comprising at least the primary determination. The external value may be obtained outside of the adjudication request.

The system for rules-driven adjudication presented above may further comprise the rules evaluator being further configured to send, for primary determinations having an indefinite outcome, an escalated request to the first client communicatively coupled to the rules evaluator, the escalated request comprising at least the adjudication request. The rules evaluator may receive a secondary determination from the first client, the secondary determination indicating the result of an evaluation of the escalated request performed by a first agent. The adjudication result may be sent to the second client in response to one of the primary determination having a definite outcome and the receipt of the secondary determination, the adjudication result comprising one of the primary determination and the secondary determination. The adjudication result may be sent in response to the receipt of a secondary determination comprising the primary determination and the secondary determination. The rules evaluator may be further configured to create a first probationary rule in response to the receipt of the secondary determination by the rules evaluator, the first probationary rule may function as an exception to a target rule, wherein the first data tag of the first probationary rule is the same as the first data tag of the target rule, the result of the first probationary rule is equal to the secondary determination, and wherein at least one of the comparator and the comparison value of the first probationary rule deviates from what is defined in the target rule to create an exception that, when applied to the adjudication request before the application of the target rule, the result is the same as the secondary determination. The rules evaluator may be further configured to store the first probationary rule within the storage, the first probationary rule further comprising a success rate. The rules evaluator may be further configured to add to the target rule a reference pointing to the first probationary rule within the storage. The rules evaluator may be further configured to apply the first probationary rule to another adjudication request resulting in the application of the target rule and the sending of another escalated request. The rules evaluator may be further configured to compare the secondary determination received in response to the another escalated request with the result of the application of the first probationary rule to the another adjudication request, and update the success rate of the first probationary rule. The rules evaluator may be further configured to refine the first probationary rule by one of modifying at least one of the comparator and the comparison value of the first probationary rule and creating a second probationary rule as an exception to the first probationary rule, in response to the first probationary rule's failure to match the secondary determination received in response to the another escalated request. The rules evaluator may be further configured to insert the first probationary rule into the appropriate rule library in response to at least one of the receipt of a manual approval and the success rate of the first probationary rule surpassing a predefined threshold. The adjudication request may be a request for prior authorization and comprise patient information, policy information, and treatment information comprising a medical code. The first client may be an insurance provider client. The second client may be a healthcare provider client. The at least one definite outcome may comprise an approval, a denial, and an indication that prior authorization is not required. The at least one indefinite outcome may comprise an indication that the system in unable to evaluate the request. The rules manager may be further configured to provide, through the network interface, an interface in which at least one rule library is formatted and through which the at least one rule library is made available to a user as a human readable resource. At least one of the first data tag and the second data tag of at least one rule in the appropriate rule library may be associated with a derived data object missing from the adjudication request and defined by an expression comprising one or more operations performed on at least one data object of the adjudication request.

According to another aspect, a method for rules-driven adjudication may comprise receiving an adjudication request through a network interface communicatively coupled to a second client through a network. The adjudication request may comprise at least one data object, each of the at least one data object being associated with a different data tag. An appropriate rule library may be identified from at least one rule library to apply the identification based at least on the adjudication request. Each of the at least one rule libraries may comprise a plurality of rules, each rule of the plurality of rules comprising a first data tag, a comparator, a comparison value, and a result returned upon satisfaction of the comparator. The comparison value may be one of a second data tag and an external value. The result may be one of an outcome and at least one subsequent rule, each outcome being one of a plurality of potential outcomes comprising at least one definite outcome and at least one indefinite outcome. The adjudication request may be evaluated and a primary determination created using a processor and a memory by applying a first rule of the appropriate rule library to the adjudication request, and using data objects from the adjudication request indicated by at least one data tag of the first rule. A first subsequent rule of the at least one subsequent rules and all logically adjacent rules within the appropriate rule library may be applied until all logically adjacent rules have been exhausted and the primary determination is an indefinite outcome or until the applying of a final rule returns an outcome that becomes the primary determination. An adjudication result may be sent to the second client through the network interface comprising at least the primary determination. The external value may be obtained outside of the adjudication request.

The method for rules-driven adjudication presented above may further comprise receiving a new rule through the network interface from a first client, and storing the new rule in one of the at least one rule library. The method may comprise sending, for primary determinations having an indefinite outcome, an escalated request to a first client through the network interface, the escalated request comprising at least the adjudication request. The method may comprise receiving a secondary determination from the first client, the secondary determination indicating the result of an evaluation of the escalated request performed by a first agent. The adjudication result may be sent to the second client in response to one of the primary determination having a definite outcome and the receipt of a secondary determination, the adjudication result may comprise one of the primary determination and the secondary determination. The adjudication result may be sent in response to the receipt of a secondary determination comprising the primary determination and the secondary determination. The method may further comprise creating a first probationary rule in response to the receipt of the secondary determination, the first probationary rule functioning as an exception to a target rule. The first data tag of the first probationary rule may be the same as the first data tag of the target rule. The result of the first probationary rule may be equal to the secondary determination. At least one of the comparator and the comparison value of the first probationary rule may deviate from what is defined in the target rule to create an exception that, when applied to the adjudication request before the application of the target rule, the result is the same as the secondary determination. The first probationary rule may be stored within a storage, the first probationary rule further comprising a success rate. A reference pointing to the first probationary rule within the storage may be added to the target rule. The first probationary rule may be applied to another adjudication request resulting in the application of the target rule and the sending of another escalated request. The secondary determination received in response to the another escalated request may be compared with the result of the application of the first probationary rule to the another adjudication request, and the success rate of the first probationary rule may be updated. The first probationary rule may be refined by one of modifying at least one of the comparator and the comparison value of the first probationary rule and creating a second probationary rule as an exception to the first probationary rule, in response to the first probationary rule's failure to match the secondary determination received in response to the another escalated request. The first probationary rule may be inserted into the appropriate rule library in response to at least one of the receipt of a manual approval and the success rate of the first probationary rule surpassing a predefined threshold. The adjudication request may be a request for prior authorization and comprise patient information, policy information, and treatment information comprising a medical code. The first client ay be an insurance provider client. The second client may be a healthcare provider client. The at least one definite outcome may comprise an approval, a denial, and an indication that prior authorization is not required. The at least one indefinite outcome may comprise an indication that the request cannot be evaluated. Each rule of the plurality of rules may be in a human-readable format. The method for rules-driven adjudication may further comprise providing, through the network interface, an interface in which at least one rule library is formatted and through which the at least one rule library is made available to a user as a human readable resource. At least one of the first data tag and the second data tag of at least one rule in the appropriate rule library may be associated with a derived data object missing from the adjudication request and defined by an expression comprising one or more operations performed on at least one data object of the adjudication request.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
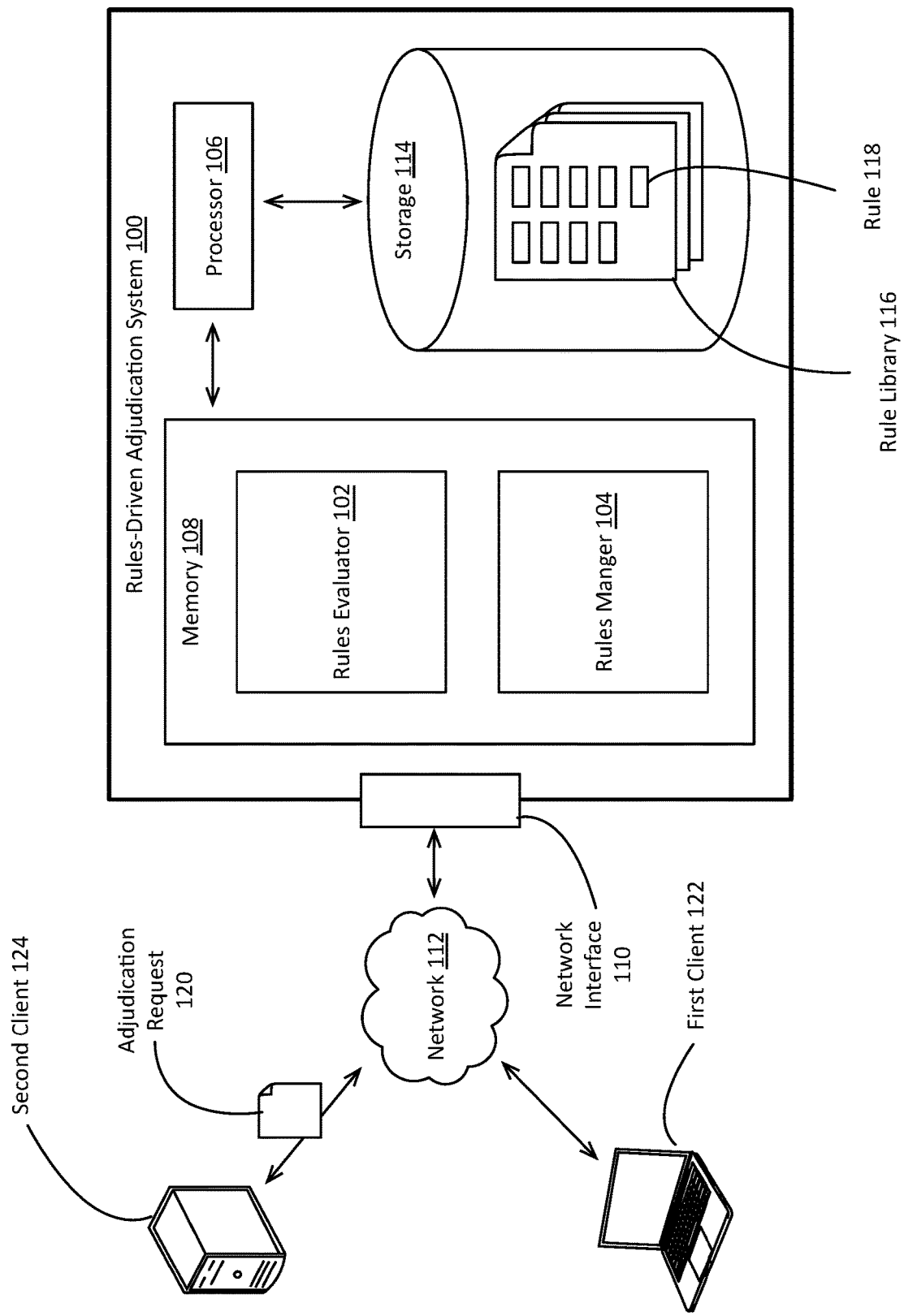
FIG. 1 is a schematic view of a rules-driven adjudication system.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

The utility of rules and policies, as a concept, is undeniable. From the laws that govern societies to the policies that ensure customer experience that is consistent throughout a nation-wide restaurant chain, the applicability of sets of rules is universal. Across a wide range of industries and endeavors, results have been improved, products have been enhanced, and efficiency increased through the application of rules and policies. The codification and use of a rule set allows for policy to be enforce fairly and with uniformity, even within a large and distributed organization. These rules help provide consistency, granting a predictability that increases overall efficiency. The creation and use of rules and policies allow entities to be more deliberate in their actions, ensuring they are better able to achieve their intended purpose.

However, the definition and application of rules is not without cost. Once defined, rules must be distributed and explained to all who will be charged with their application. Any update to the rules could require retraining an entire workforce before they are consistently applied. Additionally, the conventional method of relying on people to apply the rules, using their interpretation and judgement, introduces the possibility of deviations from the intended result. At best, people can make mistakes or misunderstand a rule; at worst, the application of rules may be tainted by bias that can be hard to prevent, let alone detect. Furthermore, complicated and/or large rule sets, such as the rules for determining prior authorization for a medical procedure, can be slow to apply, and can result in a decision making process that is sometimes opaque to the stakeholders.

Contemplated herein is a system and method for rules-based adjudication. A party or entity (hereinafter referred to as an arbiter) is able to define a series of rules that codify their intentions for a particular endeavor or determination, whether it be the fair application of employment policy, the determination of the boundaries of an insurance policy and what requires prior authorization, or even the consistent application of laws and regulations. Once defined, the rules may be applied by a rules evaluator to address a specific inquiry or request for a decision, providing immediate feedback without the need for any intermediate human intervention. The rules can be implemented and updated quickly by the arbiter, allowing the targeted activity (e.g. prior authorization, application of environmental law, etc.) to iteratively improve at a much faster pace than would be possible using conventional methods, where a workforce has to be trained and retrained on changing policies.

The rules-driven adjudication system (hereinafter "adjudication system" or simply "system") contemplated herein provides many advantages over conventional methods of rendering a decision. The adjudication system can provide a decision on a matter in a matter of seconds, rather than the hours, days, or even weeks required by conventional methods. Some embodiments of the adjudication system log every step of the evaluation of a request, which may be used to provide a reason for the decision that was rendered, a level of transparency that would otherwise be difficult or impractical to provide.

The adjudication system is advantageous over conventional methods and systems for enacting policies because it applies the rules defined by an arbiter consistently, and without bias. Furthermore, the system and method contemplated herein can enact and enforce rule sets that would be too large and/or complicated for consistent and efficient application by human agents.

For example, the policies surrounding what is and is not covered by a particular medical insurance policy for a particular condition can be complicated, and subject to misinterpretation by the humans that conventional methods rely on. An additional advantage is that, by logging each step of the adjudication process, the adjudication system facilitates oversight of the authorization process, whether by a regulator agency or by the arbiter itself.

Another advantage provided by the contemplated adjudication system and method is that it may be directly integrated with existing systems, which may reduce or even remove the need for human input of information needed to render a decision. The technology used in most industries has evolved slowly, with adoption of new technologies occurring at different rates. A consequence of this has been that, in most industries, there are entities using cutting edge technology having to interact with other entities still relying on legacy systems that can sometimes be vastly different. One example of this is the transmission of records, which could be done as digital documents shared over the internet, or sent using a fax machine. Often, a human has to bridge these gaps, introducing the potential for input errors that could lead to mistakes or delays in rendering a decision.

As a specific example, some embodiments of the adjudication system can integrate with EHR/EMR record systems in use by healthcare payers (e.g. medical insurance companies, etc.) and healthcare providers (e.g. hospitals, pharmacies, labs, etc.), ingesting patient information directly from these systems without requiring an individual to transcribe it into a web portal or paper form.

The vastly improved consistency and speed of the adjudication system and method contemplated herein, when compared to conventional methods and systems, permits the implementation of policies that are much more granular than would have been practical in the past. The rules evaluator can select and apply a set of rules in near real-time, even when that rule set considers many more factors than would be practical (i.e. able to render a decision quick enough to accomplish the intended purpose of the rules) to have a person consider in conventional methods. This improved granularity allows arbiters to implement rules with built in exceptions for situations that previously would have required additional time and effort on the part of the arbiter to handle. Some edge cases may still require human intervention; the adjudication system can automatically handle the bulk of requests, as well as recognize the edge cases and forward them on to a human representative or agent for consideration, according to various embodiments.

The systems and methods contemplated herein will be discussed in the context of a variety of use cases. It should be understood that the use cases presented herein are not intended to be limiting. The contemplated system may be applied to any industry or endeavor which makes use of rules or policies, and which would benefit from the consistent, unbiased, and transparent application of those rules to specific scenarios, providing answers in near real-time.

FIG. 1 is a schematic view of a non-limiting example of a rules-driven adjudication system 100. As shown, the system 100 comprises a processor 106 communicatively coupled to a memory 108 and a network interface 110. The memory 108 comprises a rules evaluator 102 and a rules manager 104. According to various embodiments, the rules evaluator 102 receives an adjudication request 120 and applies rules 118 drawn from a rules library 116 to render a decision. The rules manager 104 is used to define and modify the rules 118 used by the rules evaluator 102 and stored in the storage 114. The rules evaluator 102 and the rules manager 104 will be discussed in greater detail with respect to FIG. 3, below.

It should be noted that the adjudication system 100 may be implemented in a number of different computing environments. For example, in some embodiments, the adjudication system 100 may operate on a single device, such as specific computing device 900 of FIG. 9. The rules evaluator 102 and rules manager 104 may be software modules operating on a single device that has a processor 106 and a memory 108 that are preforming other operations as well. In other embodiments, the adjudication system 100, or components of the adjudication system 100, may be modules, subroutines, or components within a larger software system (e.g. part of a gateway to a private network, etc.). In some embodiments, the rules evaluator 102, rules manager 104, and/or storage 114 may exist as containers or pods in an abstracted, containerized, or virtualized system implemented on a single device or distributed over a plurality of devices (e.g. localized computing cluster, distributed cloud computing platform, etc.). In still other embodiments, the adjudication system 100 may be implemented as a node, or the components of the adjudication system 100 such as the rules evaluator 102 and the rules manager 104 may each be instantiated as nodes within a permissioned blockchain network. A blockchain network implementation will be discussed in greater detail with respect to FIG. 7, below.

Rules 118 are the core of the adjudication system 100. In the context of the present description and the claims that follow, a rule 118 is a representation of a policy specified by or on behalf of an arbiter that defines piece of logic, as well as one or more consequences of the evaluation of that logic for a specific set of circumstances. The structure of rules 118, as well as a number of specific examples, will be discussed in greater detail with respect to FIGS. 2A-2D, below.

According to various embodiments, rules 118 may be organized into one or more rules libraries 116. In the context of the present description and the claims that follow, a rules library 116 is a collection of rules 118 that are applicable for a specific context or circumstance of relevance to an arbiter. In some embodiments, rules libraries 116 may be defined based on the general type of adjudication being performed. For example, a human resources department of a corporation may define one rules library 116 for determining an appropriate disciplinary action for an employee, and another library 116 for determining candidates for internal promotion. In other embodiments, rules libraries 116 may be organized based upon an initial rule that logically splits different sets of rules that may all be directed to the same general type of adjudication. For example, a medical insurance provider may define a different rules library 116 for each healthcare provider they interact with, reflecting different policies in place for dealing with each provider based on their history (e.g. prior authorization may be required more frequently for a provider with whom the insurer has had problems within the past, etc.). In still other embodiments, all rules 118 in a system 100 may be organized in a single, universal rules library 116, relying on the evaluation of the rules 118 to direct inquiries down the correct logical path. Those skilled in the art will recognize that rules 118 may also be organized in other structures and containers known in the art.

According to various embodiments, the rules libraries 116 may be stored in a storage 114, which may be a database or other storage system known in the art. In some embodiments, rules 118 may be stored with an associated identification code or index, which can be referenced in resulting logs or transaction ledgers.

As shown in FIG. 1, a first client 122 and a second client 124 may be communicatively coupled to the adjudication system 100 through a network 112 (e.g. LAN, WAN, Internet, virtualized network, blockchain network, etc.). As will be discussed in greater detail below, in the context of the present description and the claims that follow, a first client 122 is a computing device operated by and/or associated with the arbiter (i.e. the party that defines and applies the rules), and a second client 124 is a computing device operated by and/or associated with the requestor (i.e. the party that is seeking the application of rules to a specific set of facts). The roles of the first client 122 and the second client 124 will be discussed in greater detail with respect to FIG. 3, below.

According to various embodiments, the rules evaluator 102 is configured to receive an adjudication request 120 through the network interface 110 from a second client 124. In the context of the present description, an adjudication request 120 is a data object that specifies the nature of the query and contains information pertinent to the decision. The structure and role of the adjudication request 120 will be discussed further with respect to FIG. 3, below.

According to various embodiments, the rules evaluator 102 receives adjudication requests 120, identifies an appropriate rule library within the storage 114, evaluates the adjudication request 120 and renders a determination by evaluating one or more rules 118 within the selected rule library 116. Ultimately, the rules evaluator 102 sends the result of the adjudication back to the second client 124, according to some embodiments. Additionally, according to various embodiments, the rules manager 104 is configured to allow an arbiter to define and submit new rules to be incorporated into a rules library 118. The roles of the rules evaluator 102 and the rules manager 104 will be discussed in greater detail with respect to FIGS. 3-5, below.

Figure 2A:
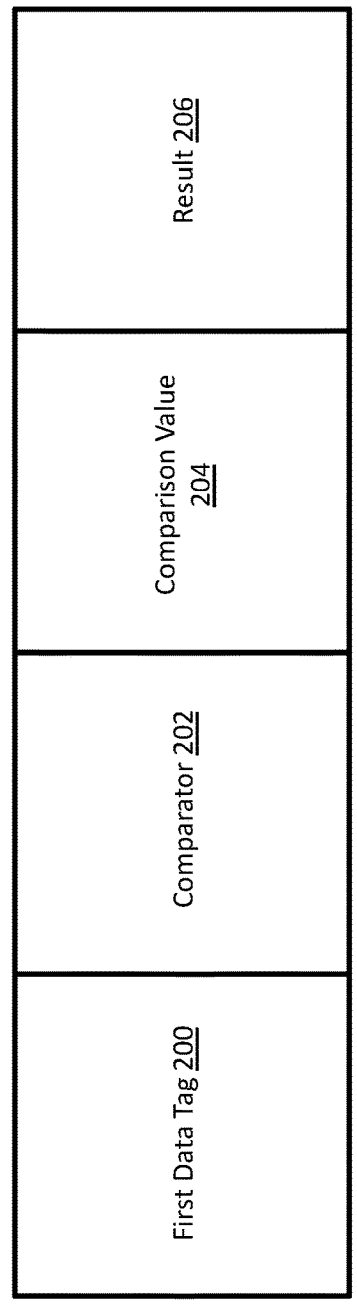
FIGS. 2A-2D are schematic views of various exemplary rules.

FIGS. 2A-2D are schematic views of various non-limiting examples of a rule 118. According to various embodiments, rules 118 may be defined using a definite structure. As shown in FIG. 2A, a rule 118 comprises a first data tag 200, a comparator 202, a comparison value 204, and a result 206, according to various embodiments. In the context of the present description and the claims that follow, a first data tag 200 is a metadata that describes the nature of a data object, such as a data object or field within an adjudication request 120. As will be discussed below with respect to FIG. 300, in some embodiments, each piece of information included with an adjudication request 120 is accompanied by a tag that indicates what that piece of information is conveying. This allows rules 118 to be defined with respect to specific pieces of information, making it simple to determine if an adjudication request 120 contains all the needed information, and also making it easy to define the rules themselves.

Figure 2B:
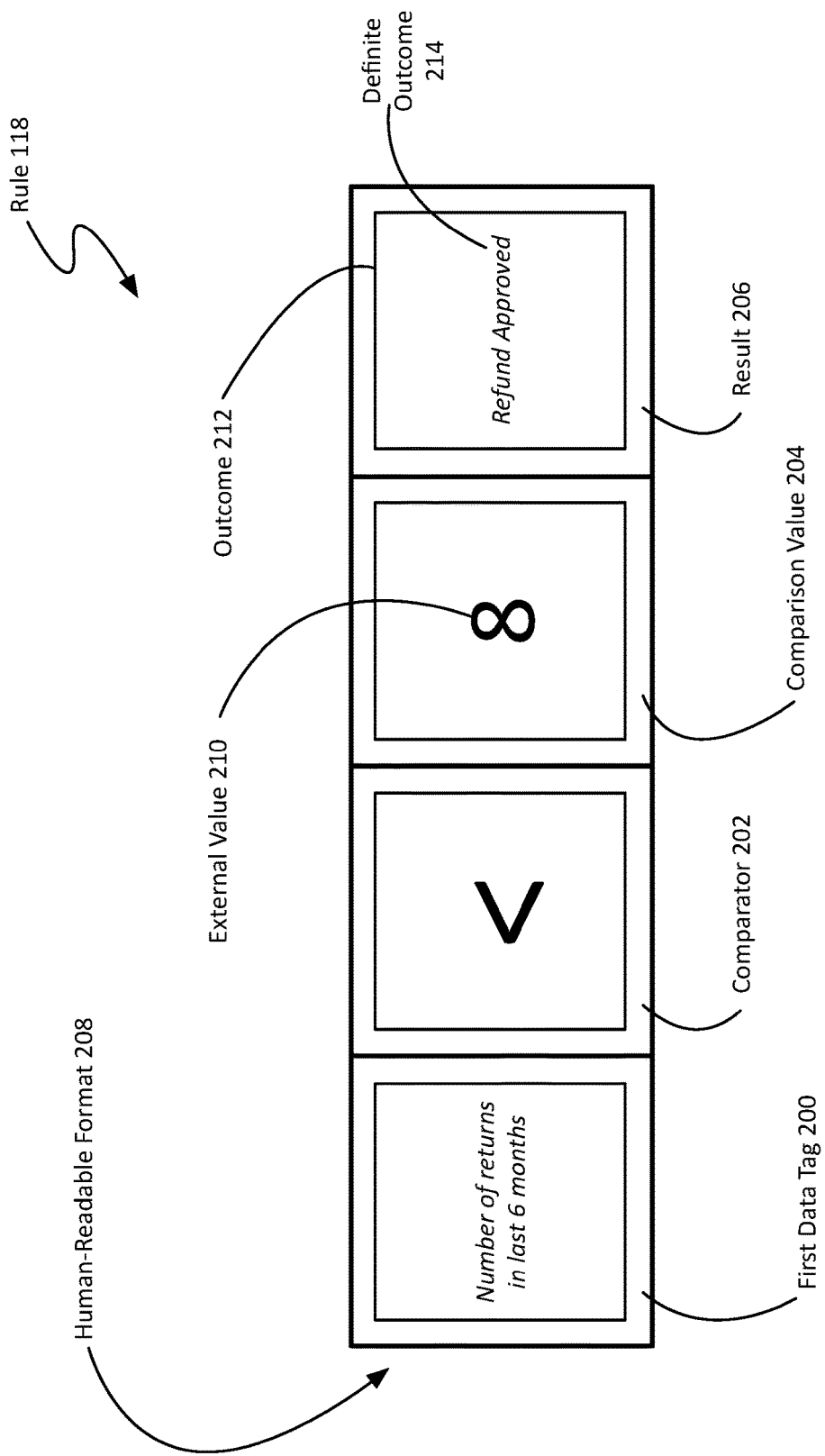
Figure 2C:
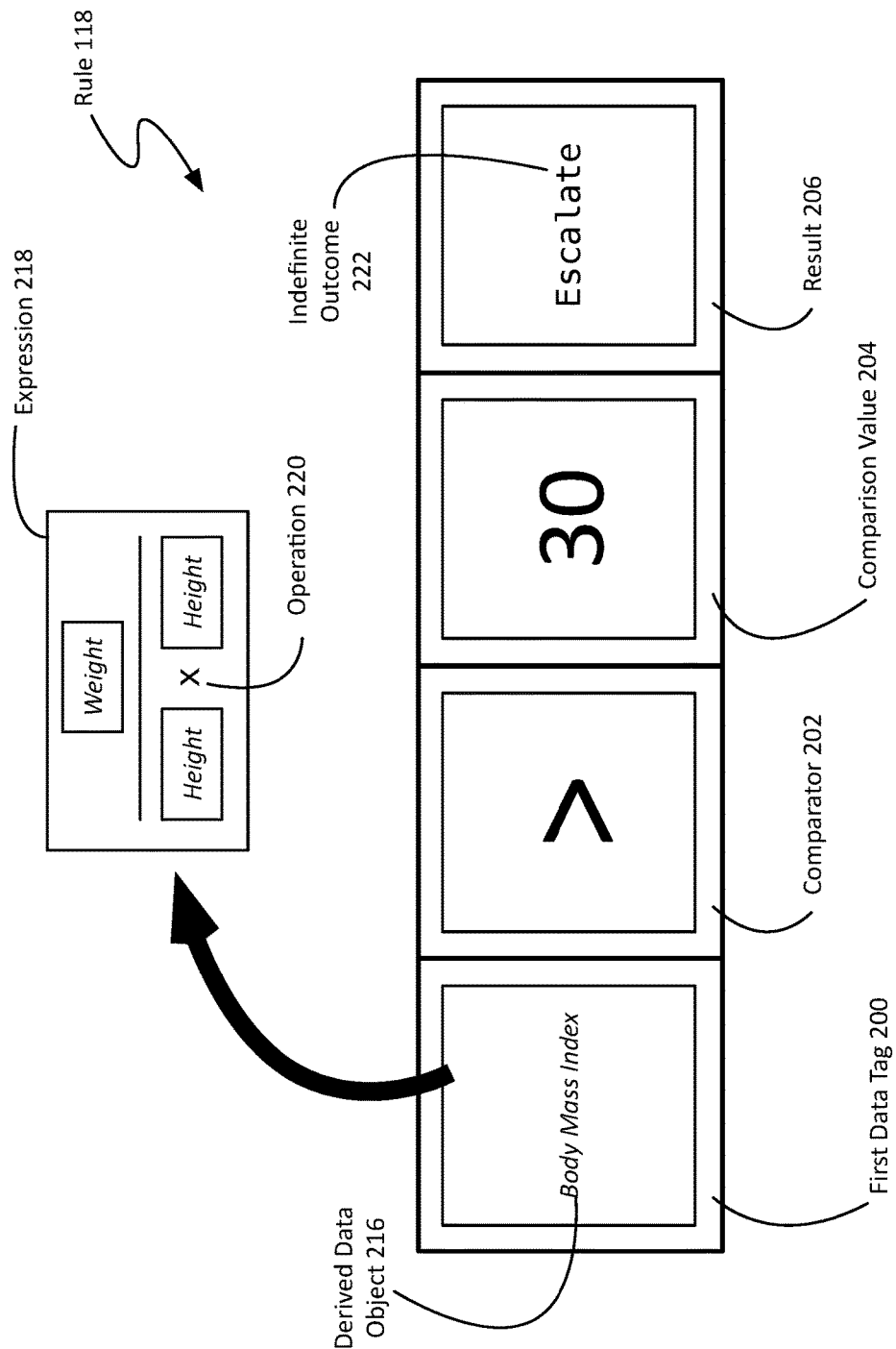
Figure 2D:
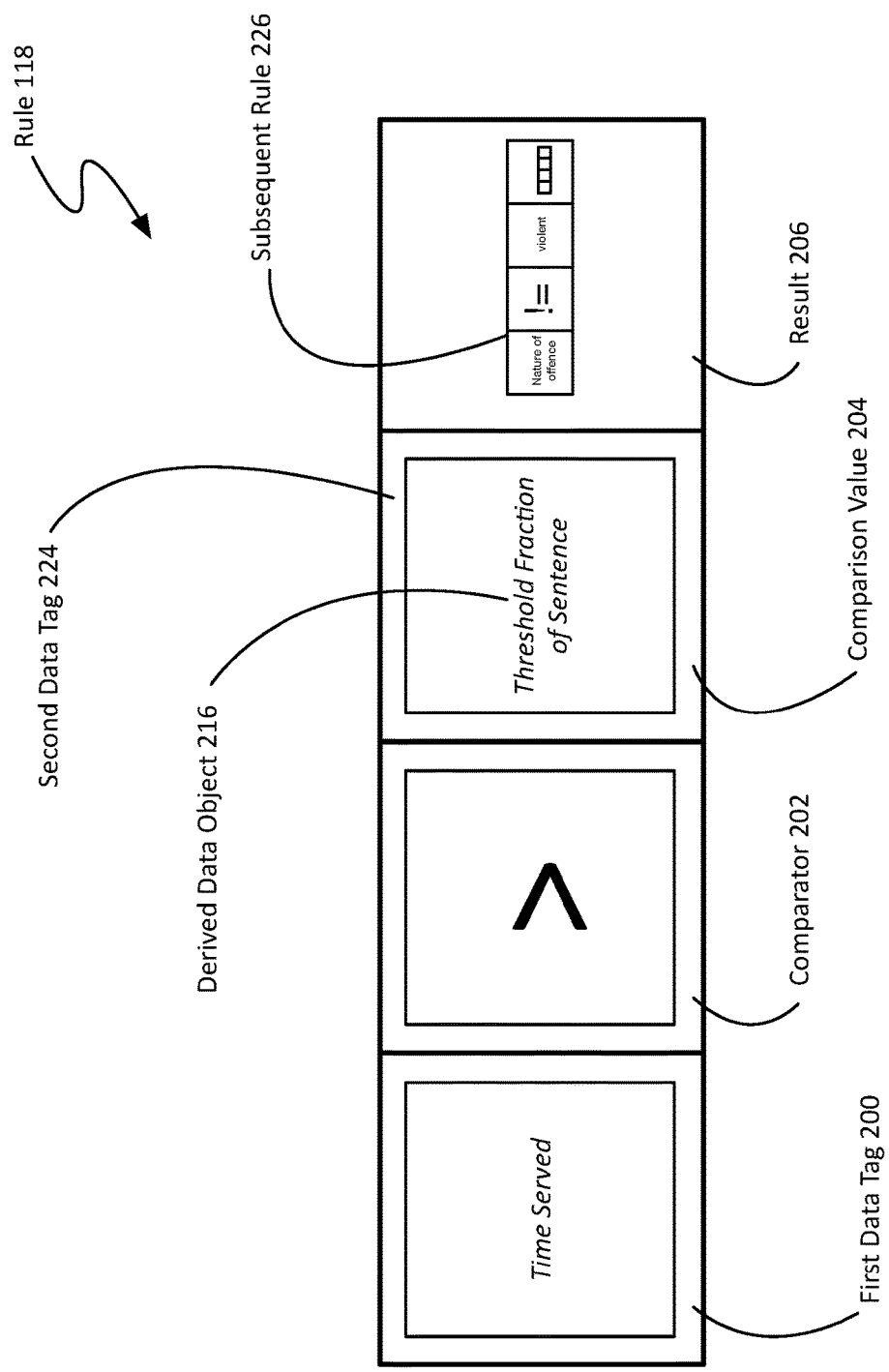

As shown in FIGS. 2B-2D, examples of data tags include, but are not limited to, "Number of returns in last 6 months", "Body Mass Index", "Time Served", and "Threshold Fraction of Sentence". According to various embodiments, a first data tag 200 may refer to a data object 300 found within an adjudication request 120, but in some embodiments, it may also refer to a derived data object 216 which, while not explicitly included within an adjudication request 120, can be derived from data objects 300 included within the adjudication request 120.

In the context of the present description and the claims that follow, a comparator 202 is a symbolic representation of a relation between two objects, values, entitles, or the like. For example, the relationship between a first data tag 200 and a comparison value 204. Examples include, but are not limited to, greater than, greater than or equal, less than, less than or equal, equal, not equal, belongs to the set of (a discrete set), does not belong to the set of (a discrete set), is between (two discrete values), is not between (two discrete values), is within a range that is closed/open/both (e.g. (a,b), [a,b], (a,b], [a,b), etc.), intersects with, does not intersect with, is orthogonal to, and the like.

In the context of the present description and the claims that follow, a comparison value 204 is a value with which the first data tag 200 is being compared with, per the comparator 202. In some embodiments, the comparison value 204 has a single value, while in other embodiments the comparison value 204 may have two values. For example, when determining if the first data tag 200 is between two values or within a range, two values may be passed along in the comparison value 204. In still other embodiments, the comparison value 204 may have three, four, or more values. For example, in one embodiment, when determining if the adjudication request 120 has a data object having the first data tag 200 belongs to a set of seven different values, the comparison value 204 could have seven values, or could refer to seven values.

In some embodiments, the comparison value 204 may be a second data tag 224, as shown in FIG. 2D. The second data tag 224 may resolve to another data object 300 within the adjudication request 120. In some embodiments, the second data tag 224 may be associated with a derived data object 216, which will be discussed further, below.

In some embodiments, the comparison value 204 may be an external value 210, as shown in FIG. 2B. In the context of the present description and the claims that follow, an external value 210 is a value that is obtained outside of the adjudication request 120. The external value 210 may have any form used by a data object within the adjudication request 120 including, but not limited to, a single value, a series of values, a range, a binary file (e.g. image, sound, etc.), and the like. In some embodiments, the external value 210 contained within a rule 118 may be the actual value (i.e.

'3' in FIG. 2B), while in other embodiments an external value 210 may refer to said value, similar to a data tag, except entirely directed outside of the adjudication request 120. For example, an external value 210 may refer to a value or values that is/are obtained from a third party server, or from elsewhere within the storage 114. As a specific example, in one embodiment, an external value 210 may refer to a quantity specified in a statute, used in a rule designed to ensure adjudications are in compliance with said statute.

As previously discussed, data tags such as the first data tag 200 and the second data tag 224 may refer to data objects within an adjudication request 120. In some embodiments, a data tag may refer to a derived data object 216. In the context of the present description and the claims that follow, a derived data object 216 is a data object that is missing from the adjudication request 120 and that is instead defined by an expression 218 comprising one or more operations 220 performed on at least one data object 300 (or the value or values contained within said data object) of the adjudication request 120. As a specific example, as shown in FIG. 2C, a rule 118 that is part of determining prior authorization for a medical procedure may take into account a patient's body mass index, or BMI. The BMI may not be an actual data object within the adjudication request 120, but is instead defined by an expression 218 that is referenced by the "BMI" data tag. That expression gives the formula for calculating BMI, weight divided by height squared; weight and height are both data tags that point to data objects that are contained within the adjudication request.

In some embodiments, a data tag that resolves to a derived data object 216 may be unique to the derived data object 216, while in other embodiments, it may also refer to a data object within an adjudication request 120. Continuing with the specific, yet non-limiting example, of FIG. 2C, those prior authorization rules may be defined for use with multiple healthcare providers, each having a different EMR system. One provider may include BMI in the records they submit within an adjudication request 120, while the other provider may only provide weight and height. In some embodiments, a data tag may be first sought after within the adjudication request 120, and then sought after among defined derived data objects if not found within the adjudication request 120. In other embodiments, the derived data object associated with a data tag may always be given precedence.

As shown in FIG. 2C, the expression 218 of a derived data object 216 may be a mathematical formula with data tags as placeholders and symbols representing various mathematical operations 220 (e.g. +, x, etc.). In some embodiments, the expression 218 may be a series of simple operations 220, while in other embodiments, the expression 218 may comprise more complicated branching logic and evaluations. In some embodiments, a derived data object may comprise an expression 218 that is machine-readable and evaluable, but may not necessarily be human readable. The human-readability of rules and their components will be discussed in greater detail below.

In the context of the present description and the claims that follow, saying that a data tag is "associated with" a data object means that specific tag is uniquely linked to a particular object tied to that specific tag through some sort of structure (e.g. contiguous memory address, data type, indexed reference, etc.), effectively describing the information within the object in some way. According to various embodiments, a data tag may be used as a placeholder for said information when formulating a rule or other reference that is to be applied to a variety of adjudication requests 120 that each contain said data object, or contain one or more data objects used to derive said data object, albeit possibly having a variety of values. Within the context of an adjudication request, a data tag should be unique, only referring to a single data object within the adjudication request.

In the context of the present description and the claims that follow, a result 206 is the value returned, or the action taken, in response to the comparison, defined by the comparator 202, between the first data tag 200 and the comparison value 204 being satisfied. In some embodiments, the result 206 may be an outcome 212, while in other embodiments, it may refer to another rule to be applied.

An outcome 212 is a predefined result that is returned after evaluation of an adjudication request 120. According to various embodiments, a rules library 116 may be defined to have a plurality of potential outcomes 212 that may be returned after evaluating a request. An outcome 212 may be a definite outcome 214, meaning the adjudication arrived at an answer, and an indefinite outcome 222, meaning the adjudication was not able to arrive at a determination. FIG. 2B shows a non-limiting example of a definite outcome 214, "Refund Approved". Other examples include, but are not limited to, "approved", "denied", "yes", "no", and the like.

FIG. 2C shows a non-limiting example of an indefinite outcome 222, "escalate". According to various embodiments, the rules evaluator 102, when not able to come to a definite conclusion, or when there are no more rules to apply, will return an indefinite outcome 222. In some embodiments, when the evaluation of a rule 118 returns an indefinite outcome 222, that indefinite outcome 222 is returned as an adjudication result, indicating to the requesting party that the determination will have to be made using other means (e.g. prior authorization will need to be requested using conventional methods, etc.). In other embodiments, when the evaluation of a rule 118 returns an indefinite outcome 222, the adjudication request 120 and the indefinite outcome 222 may be sent for evaluation by a human agent, or using some other mechanism. In still other embodiments, both options may be available, and the path taken may be indicated by the indefinite outcome 222 itself. As a specific example, FIG. 2C shows a case where, if the patient has a BMI over 30, the adjudication request 120 should be escalated for evaluation by a human agent. Adjudication results and agents will be discussed in greater detail with respect to FIG. 3, below.

It should be noted that an outcome 212, in some embodiments, may comprise a value indicating the result, such as a string containing "prior authorization granted". In other embodiments, outcomes 212 may contain values that refer to outcomes enumerated elsewhere, such as within the rules library 116. As a specific example, outcome number 002 could resolve to "disciplinary action is not warranted" within a rule library 116 created to ensure human resources policy is followed when dealing with employee infractions.

As stated above, the result 206 of every rule 118 in a rules library 116 is either an outcome 212 or one or more subsequent rules 226. In the context of the present description and the claims that follow, a subsequent rule 226 is a rule that is evaluated as the result of the satisfaction of another rule 116. See, for example, FIG. 2D, which shows a non-limiting example of a rule 118 from a rules library 116 for determining if a prisoner is eligible for a particular benefit, whether it be a favorable assignment or consideration for parole. The rule shown in FIG. 2D states that if the "Time Served" is greater than or equal to a "Threshold Fraction of Sentence" (a derived data object 216 based on a sentence data object and a threshold constant that is an external value), then a subsequent rule 226 should be evaluated. The structure of a rule library 116 and the process of moving from one rule 118 to a subsequent rule 226 or a logically adjacent rule will be discussed in greater detail with respect to FIG. 4.

In some embodiments, the result 206 of a rule 118 may comprise the entirety of one or more subsequent rules 226 (including their subsequent rules 226, and so forth). In other embodiments, a subsequent rule 226 may be indicated as the result 206 referentially, calling out the subsequent rule 226 using an identifier, memory pointer, record index, or some other method known in the art that uniquely identifies that particular rule or rules.

According to various embodiments, the rules 118 are stored in a human-readable format 208. In the context of the present description and the claims that follow, a human-readable format 208 is a format that conveys the elements of a rule using a natural or ordinary language, meaning a language that has evolved naturally in humans. For example, in FIG. 2B, "Number of returns in last 6 months" could be the value of a data tag that points to a data object in the adjudication request that indicates the number of returns that customer has made in the last six months. The use of human-readable formatting 208 still means that tags must be unique, to prevent confusion and erroneous determinations. In some embodiments, a rule 118 or even an entire rule library 116 may be stored using a JSON format.

The use of a human-readable format is advantageous over other systems for a number of reasons. First, it facilitates the creation and modification of rules by those responsible for making such a decision, rather than requiring a programmer to function as an intermediary. Also, using a human-readable format 208 increases transparency; an individual can look over a log of each rule evaluation that led to a particular result and see exactly what was considered and with what criteria. Furthermore, as will be discussed further with respect to FIG. 3, in some embodiments a rules library 116 may be made available as a browsable reference, allowing people to see all of the rules, as they are defined, and how they carry out various policies of an organization. Any update made to the rules 118 would be immediately reflected in this browsable reference, unlike conventional systems and methods.

Another advantage of storing the rules 118 in a human-readable format 208 is that the rules are evaluated at runtime, rather than precompiled and static at runtime, according to various embodiments. Allowing the rules 118 to be defined as data (in a human-readable format 208), changes to rules or a rule library may be made while the rule evaluator is operating, allowing them to be defined or redefined at runtime, resulting in an agile system that can quickly adapt to changes in regulation, policy, or goal, without recompiling or significant interruption to operation.

It should be noted that, while some embodiments of the system 100 may utilize rules 118 having the structure discussed above, other embodiments may employ rules 118 having an alternate structure. For example, in some embodiments, an adjudication system 100 may be employed in circumstances where all considerations to be made in applying a policy are made by determining if a piece of data is less than or equal to a particular quantity. In such an embodiment, there may be no need to specify a comparator 202 in each rule 118, since it would always be the same. As another example, in some embodiments, the rules library 116 may be structured such that the rules 118 implicitly reference each other by their relative position, and that some rules may simply define a constant, which serves as a result. In such an embodiment, the rules 118 could be defined without explicitly specifying the result 206 as a portion of the rule 118, as that could be implemented by the relative position of the rules 118 within the library 116. Those skilled in the art will recognize that still other structures may be employed in defining rules 118 that may be applied by a properly configured rules evaluator 102.

Figure 3:
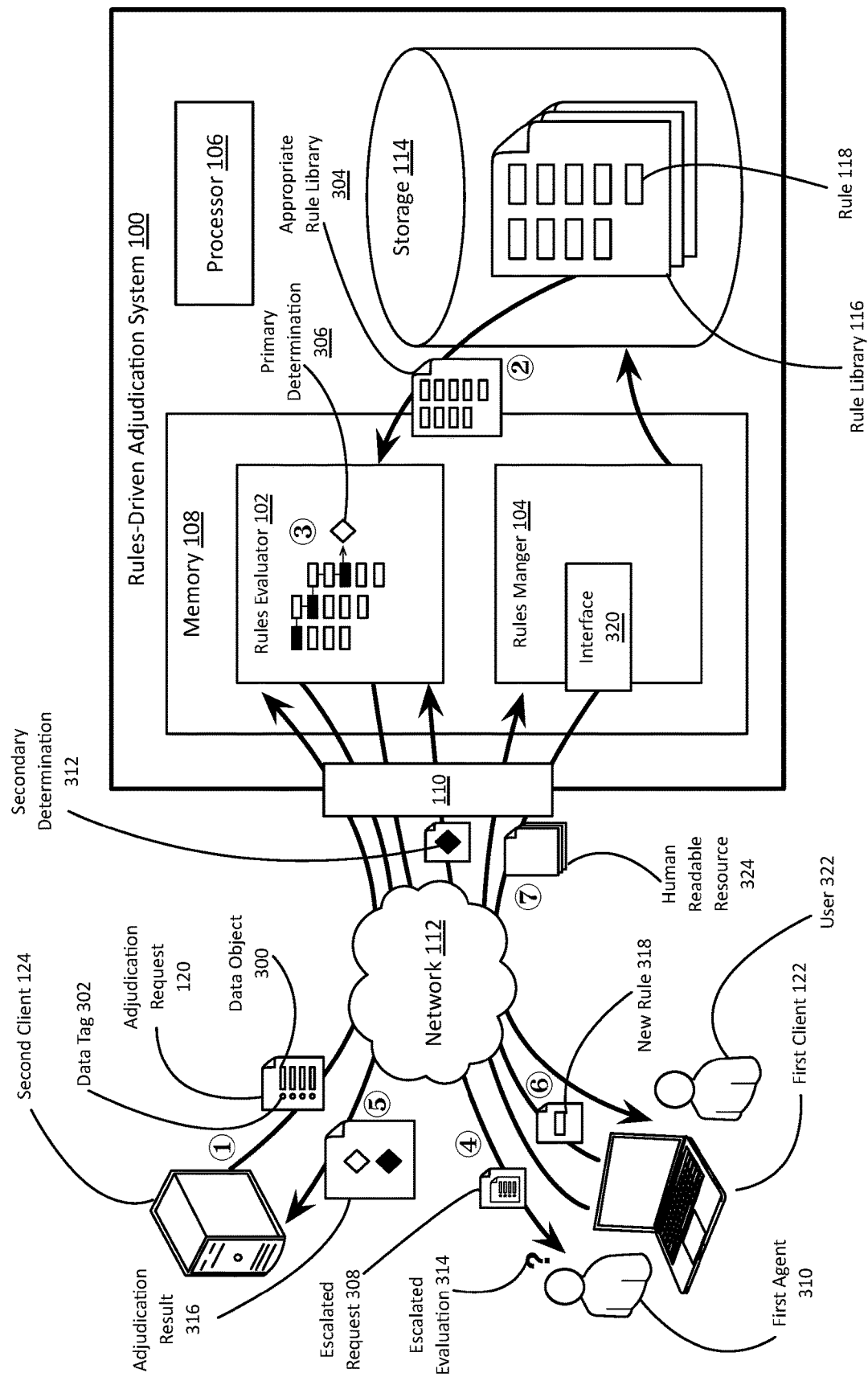
FIG. 3 is a process view of a rules-driven adjudication system

FIG. 3 is a process view of a non-limiting example of a rules-driven adjudication system 100. As shown, an adjudication request 120 is received by the rules evaluator 102 through the network interface 110 from a second client 124. See circle '1'. As previously stated, a second client 124 is a computing device operated by and/or associated with the requestor (i.e. the party that is seeking the adjudication). According to various embodiments, the adjudication request 120 comprises the information that will be needed to perform the requested adjudication, partitioned within the adjudication request 120 as at least one data object 300. The data object 300 may be in any form known in the art for storing information, which may itself be a single piece of information, a series, a range, a matrix, a binary file (e.g. an image, a sound, a movie, etc.), or any other type of data known in the art. Each data object 300 has an associated data tag 302 that identifies the nature of the information contained, so that it may be retrieved when needed by the application of a rule 118 by the rules evaluator 102. According to various embodiments, at least the tags 302 will be in a human-readable format. Additionally, in some embodiments, the adjudication request 120 also indicates the desired adjudication, when a rules evaluator 102 is configured to execute more than one type of adjudication, whether by having access to more than one rule library 116, or through a rule library 116 that is constructed for use in more than one type of adjudication (e.g. determining prior authorization for a medical procedure as well as determining a patient's responsibility, etc.).

Next, the rules evaluator 102 identifies an appropriate rule library 304 from the one or more rule libraries 116 stored in the storage 114. See circle '2'. In the context of the present description and the claims that follow, an appropriate rule library 304 is a rule library 116 that matches at least the adjudication being requested. In some embodiments, determining the appropriate rule library 304 may also take into account who is making the request (i.e. the requestor) and/or of whom that request has been made (i.e. the arbiter). For example, in some embodiments, a rules evaluator 102 may be configured to evaluate adjudication requests 102 seeking a decision on behalf of more than one party or arbiter. As a specific example, within a permission blockchain network, multiple insurance companies may exist as organizations within the blockchain network, each having requests automatically processed using rules specific to each company, but evaluated by a shared rules evaluator node. Operation within a permissioned blockchain network will be discussed in greater detail with respect to FIG. 7.

Additionally, the identity of the requesting party may influence which rule library 116 is the appropriate rule library 304. As a specific example, an insurance company may have worked out different deals with different providers, and the way an adjudication is evaluated may depend on who is rendering the desired treatment.

In other embodiments, an appropriate rules library 304 may be identified by matching a predetermined data object 300 within the adjudication request 120 that, due to the nature of requests being made of the system 100, is indicative of a specific group of rules 118. As a specific example, in an embodiment used to evaluate if decisions are in compliance with human resource policies, the appropriate rule library 304 may be chosen based upon the particular department where the employee works, rather than the department making the request.

Next, the rules evaluator 102 evaluates the adjudication request and creates a primary determination 306. See circle '3'. The process of how the rules evaluator 102 applies the rules 118 of a rules library 116 to evaluate an adjudication request 120 will be discussed with respect to FIG. 4, below. The primary determination 306 (i.e. the white diamond in FIG. 3) is the outcome 212 that is the result of the rules evaluator 102 applying a rules library 116 to the adjudication request 120.

In the case of the rules evaluator 102 running out of rules 118 to apply, or otherwise not being able to make the determination requested, the primary determination 306 will be an indefinite outcome 222. As previously stated, in some embodiments, upon the arrival at an indefinite outcome 222, the rules evaluator 102 may return the indefinite outcome 222 to the second client 124 as an adjudication result 316, informing the requestor that another method should be used.

In other embodiments, including the non-limiting example of FIG. 3, if the rules evaluator 102 arrives at a primary determination 306 having an indefinite outcome 222, or an indefinite outcome 222 that explicitly requests escalation, an escalated request 308 is sent to a first client 122 that is communicatively coupled to the rules evaluator 102. See circle '4'. According to various embodiments, the escalated request 308 comprises at least the adjudication request 120. In some embodiments, the escalated request 308 may also include a log of the various rules 118 applied by the rules evaluator 102, and the results of each application, that culminated in the arrival at an indefinite outcome 222. In some embodiments, the rules evaluator 102 may transform the escalated request 308 into a format compatible with whatever process or system is employed by the arbiter (e.g. an electronic format required by an insurance company for electronically submitted inquiries about coverage to be evaluated with conventional methods, etc.).

As previously stated, a first client 122 is a computing device operated by and/or associated with the arbiter (i.e. the party that defines and applies the rules). In this case, the first client 122 is operated by a human agent 310, who receives and evaluates the escalated request 308. In the context of the present description and the claims that follow, a human agent 310 is an individual authorized by the arbiter to make determinations like the determination being requested of the system 100. For example, in some embodiments, the human agents 310 may be the individuals who previously made all determinations under a conventional system. Advantageously, using the systems and methods contemplated herein, these skilled agents can focus their attention on the edge cases that are not able to be handled by the rules library 116, as defined at that time. An adaptive library will be discussed with respect to FIG. 5, below.

The agent 310 makes an evaluation of the escalated request 308, and sends, through the first client 122, a secondary determination 312 indicating the result of the evaluation 314 back to the rules evaluator 102. Then, the rules evaluator 102 sends an adjudication result 316 back to the second client 124 through the network interface 110. See circle '5'. According to various embodiments, the adjudication result 316 comprises at least a primary determination 306. In embodiments that make use of escalated requests 308, the adjudication result 316 may contain the secondary determination 312.

In some embodiments, the return of secondary determinations 312 may be accompanied by the primary determination 306. As an option, in some embodiments, the adjudication result 316 may also comprise a log of the rules applied, and their results, giving a level of transparency to the adjudication not typically found in conventional systems and methods. Also, in some embodiments, the adjudication result 316 may be transformed before sending to the second client 124, putting the result 316 in a format compatible with the requestor's system (e.g. EMR/EHR systems, proprietary systems, etc.).

As shown, the adjudication system 100 also comprises a rules manager 104. The rules manager 104 is the interface through which an arbiter, or an agent 310 of the arbiter, may define a new rule 318, update a rule 118 or a rules library 116. See circle '6'. In some embodiments, the agent 310 may interact with the rules manager 104 through the first client 122, using any method known in the art, including but not limited to an API, a web interface, an application, and the like. Once a new rule 318 has been defined by the agent 310, and received and stored within a rules library 116 by the rules manager 104, no further human interaction is needed, unless the arbiter would like to update the rule.

As previously mentioned, an additional advantage to storing the rules 118 in a human-readable format 208 is that the rules library 116 may be used as a reference. According to various embodiments, the rules manager 104 is further configured to provide, through the network interface 110, an interface 320 in which at least one rule library 116 is formatted and through which the at least one rule library 116 is made available to a user 322 as a human readable resource 324. See circle '7'.

Storing the rules 118 in a format 208 that is both human readable as well as machine consumable allows the rules 118 to serve as both a reference to individuals associated with the arbiter, requestor, or other party, while still being actionable within the rules evaluator 102. Conventional adjudication methods and workflows have resulted in fragmented and easily outdated specifications of policies that make it difficult for requestors and other individuals to perform research or anticipate an adjudication. In some embodiments, the rules 118 are stored in a format 208 that is simultaneously human readable and machine consumable (for execution/evaluation). In other embodiments, the rules 118 may be stored in a format that is machine-consumable while also being easy to make available in natural language. For example, in one embodiment, the rules 118 may be stored in a data structure such as JSON or XML that is easily transformed into natural language using natural language templates that describe the structure implied by the data structure, and that have placeholders where the rule elements may be inserted, making them human readable.

According to various embodiments, an adjudication system 100 may be employed in applying the rules of multiple organizations that may be serving a common pool of customers or entities. For example, a rules driven adjudication system 100 may be implemented within a permissioned blockchain network facilitating interactions between multiple insurance companies, hospitals, labs, and other healthcare providers. Such an example will be discussed in greater detail with respect to FIG. 7, below. The adjudication system 100 may be utilized to evaluate prior authorization requests coming from different hospitals, whose patients may have a variety of insurances that are represented within the blockchain network. Each medical insurance company would have their own set of policies, disclosed in their own format and structure. Such a variety of policies and policy formats would quickly bog down conventional methods for applying multiple rule sets to different cases. According to various embodiments, the system 100 contemplated herein is able to quickly ingest these diverse and inconsistent sets of rules from formats and media that was intended for human consumption (e.g. formatted PDF documents, scanned paper literature, etc.). Once ingested, the system 100 places the rules 118 into a standardized format that is easy to digest for people as well as computers.

The rules 118 defined within a rules library 116 can serve as a concise, up-to-date reference 324 for humans, and as instructions for providing nearly instantaneous responses to adjudication requests. The rules manager 104 provides some form of interface 320 (e.g. SDK, web, REST API, etc.) through which authorized individuals may access the rules 118 as a reference, according to various embodiments. In some embodiments, the rules 118 may be presented without modification, while in other embodiments, the rules 118 may be inserted into a template with little to no modification, the template providing the connective tissue that puts the rules into natural human language. This approach to storage and presentation may also facilitate the translation of rules into different languages, as most of the elements of a rule are nouns (e.g. measurement, medical test, time span, etc.), one of a limited set of comparators, and an outcome, according to various embodiments. Because of this predictable, consistent format and structure, a good translation may be obtained quicker, and with less effort, than would be required translating the rules 118 in their original format.

Figure 4:
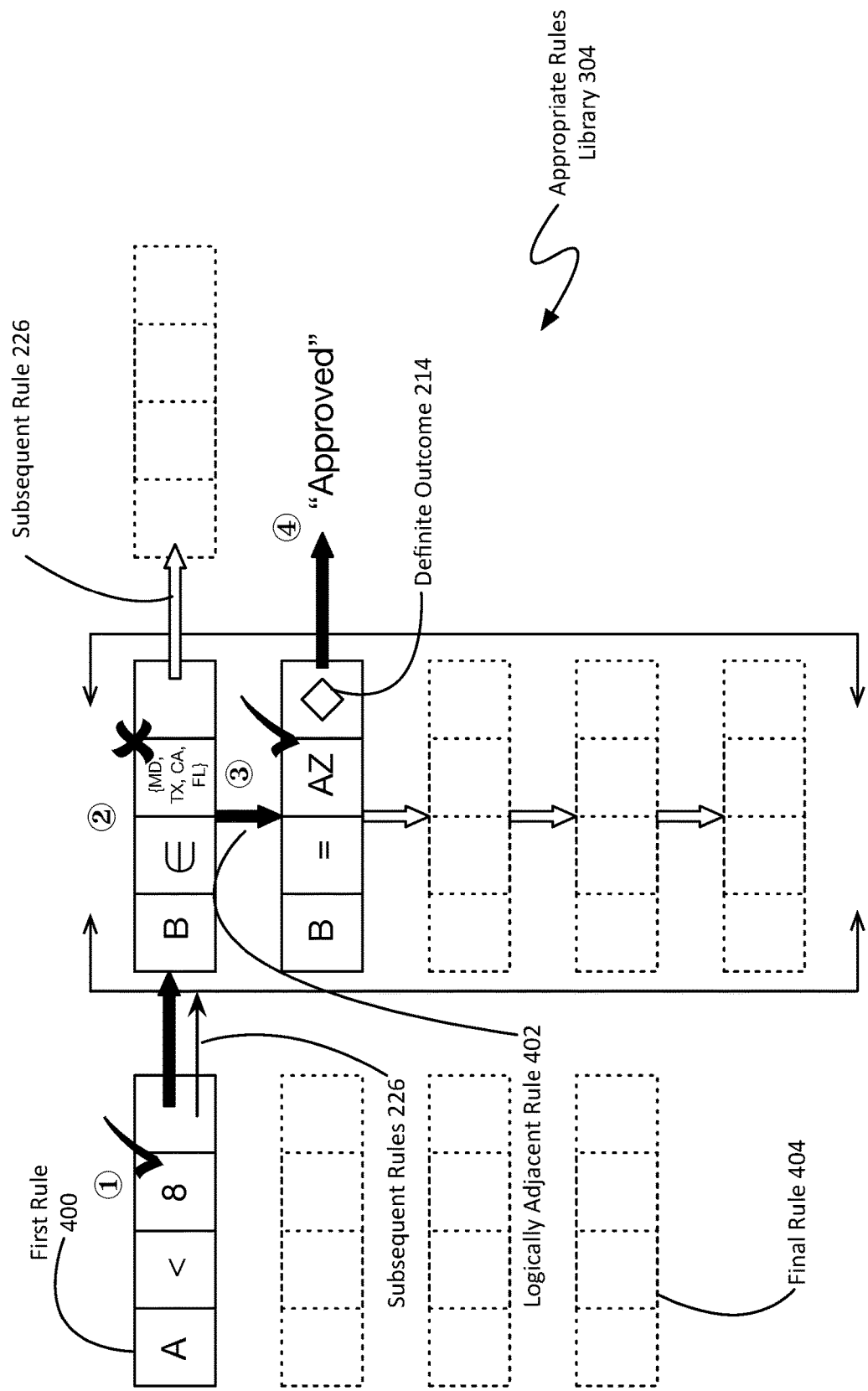
FIG. 4 is a process view for a rules-driven adjudication system applying a rule library.

FIG. 4 is a process view for a non-limiting example of a rules-driven adjudication system 100 applying a rule library 116. According to various embodiments, the rule evaluator 102 evaluates the adjudication request 120 and creates a primary determination 306 by applying a first rule 400 of the appropriate rule library 304 to the adjudication request 120. See circle '1'. The first rule 400 is a rule 118 within a rules library 116 that has been designated the starting point for the evaluation of an adjudication request 120. Typically, the first rule 400, or even the first tier of rules, is chosen to quickly rule out a large number of potential paths through the rules library 116. As shown, in this non-limiting example, the first rule 400 asks if the data object 300 represented by the data tag 302 'A' is less than 8. Upon determining that it is, the result of this first rule 400 is a collection of subsequent rules 226, which are to be applied next.

According to various embodiments, the application of rules continues, applying subsequent rules 226 upon satisfaction of a comparator or a logically adjacent rule 402 upon failure. Continuing with the non-limiting example of FIG. 4, next the first subsequent rule is applied, which asks if the data object 300 represented by the data tag 302 'B' belongs to the set {MD, TX, CA, FL}. See circle '2'. The adjudication request 120 does not satisfy this rule, so the evaluator 102 moves on to the next logically adjacent rule 402. See circle '3'.

In the context of the present description and the claims that follow, a logically adjacent rule 402 is a relative description for a rule. Upon application of a first rule to an adjudication request 120, and that first rule is determined to not be satisfied, the logically adjacent rule 402 of the first rule is the rule that gets applied next, after the first rule fails. The non-limiting example of a rules library 116 shown in FIG. 4 has organized the rules sequentially, with the logically adjacent rules 402 being beneath the rule that precedes them in application.

The application of rules continues until an outcome is returned (see circle '4'), all logically adjacent rules 402 have been exhausted resulting in a primary determination 306 that is an indefinite outcome 222, or the applying of a final rule 404 returns an outcome that becomes the primary determination 306. In the context of the present description and the claims that follow, a final rule 404 is a rule 118 within a rule library 116 that applies to all adjudication requests 120 that do not trigger any other rules, including the first rule 400. It serves as a default response. In some embodiments, it may be a unique indefinite outcome 222, indicating that no determination could be made because it was an unforeseen set of circumstances. In other embodiments, a rules library 116 may not have a catch-all final rule 404, and instead return indefinite outcomes when all logically adjacent rules have failed.

In some embodiments, the order in which rules are applied may be important. For example, in some embodiments, the rules that are subsequent rules to a preceding rule may be ordered to place rules with narrow conditions before rules with broad conditions, allowing the early rules to be defined as exceptions to the later rules. As a specific example, a first rule could determine if a data object is between 3 and 5. The logically adjacent rule to this first rule could be defined in two ways: first, it could determine if the data object is in the range from 1 to 3 or from 5 to 8, or it could ask if the object is in the range from 1 to 8, relying on the fact that it would have already failed to be found between 3 and 5. The definition of rules that are applied as exceptions to the logically adjacent rules are easier to amend with new rules, particularly rules that may be developed automatically by the system 100, as will be discussed with respect to FIG. 5. However, the definition of self-sufficient rules may be easier to present to users 322 as a human readable resource 324 provided through the rules manager 104, as previously discussed.

Figure 5:
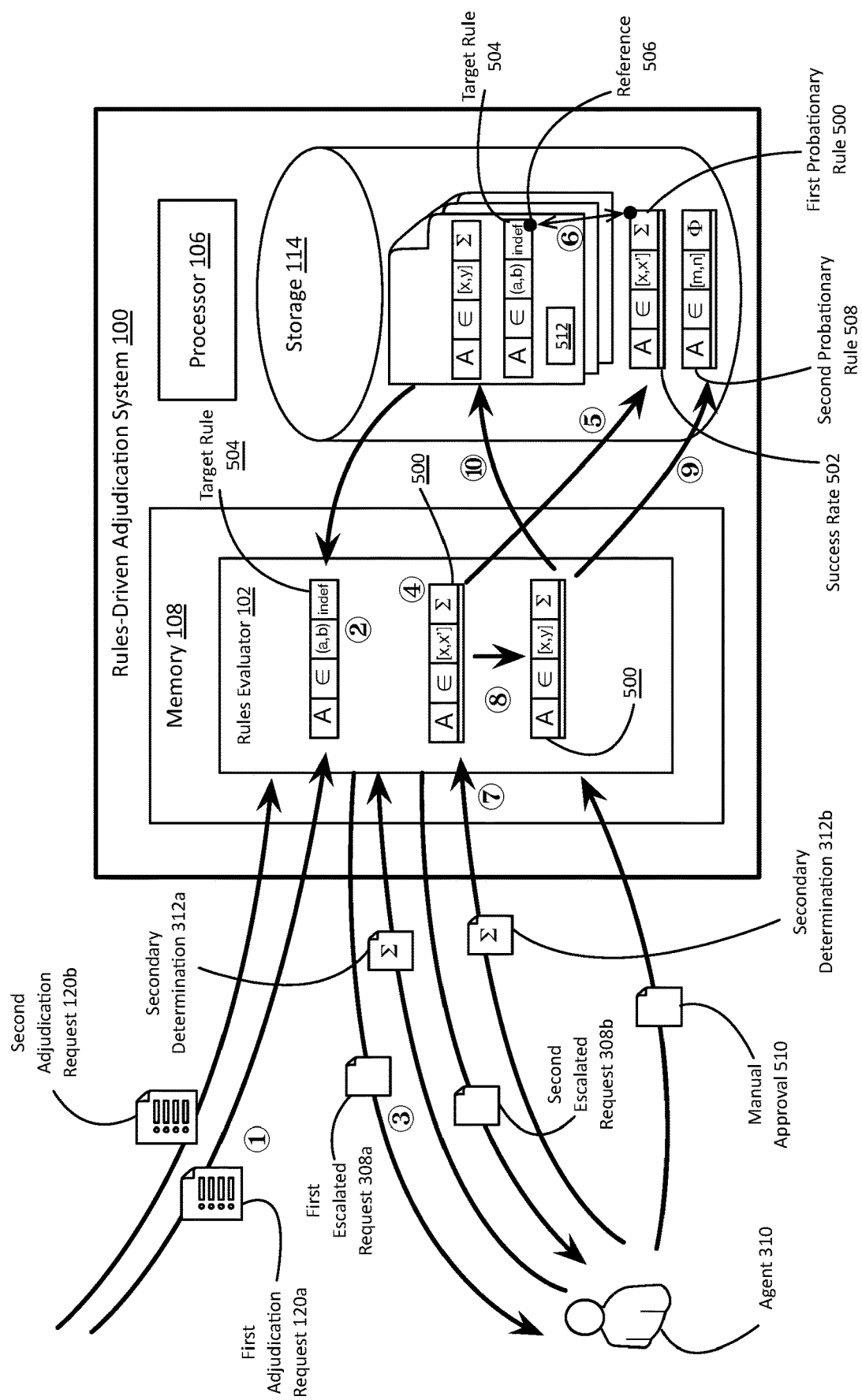
FIG. 5 is a process view for a rules-driven adjudication system learning a new rule by observation.

FIG. 5 is a process view for a non-limiting example of a rules-driven adjudication system 100 learning a new rule 318 through observation. In some embodiments, the adjudication system 100 may suggest to an arbiter the potential need for new or updated rules 118, by observing judgments rendered by human agents 310 in edge cases and cases which have no defined rules 118 (e.g. cases that reach a final rule 404, etc.). It should be noted that various elements of the system 100 and the context in which it operates, such as the network adapter 110, the network 112, the clients, and the rules manager 104, have been omitted from FIG. 5 for clarity. These omissions should not be interpreted as limitations.

As shown in FIG. 5, a first adjudication request 120a has been received by the rules evaluator 102 (circle '1') and a rule has been evaluated that resulted in an indefinite outcome 222 (circle '2'). According to various embodiments, the process for automatically creating a new rule begins when a first escalated request 308a is sent and a secondary determination 312a is made by an agent 310 in response to the first escalated request 308a. See circle '3'. As the process discussed above continues (e.g. the adjudication result 316 is sent to the second client, not shown), a first probationary rule 500 is created in response to the receipt of the secondary determination by the rules evaluator 102. See circle '4'.

According to various embodiments, the first probationary rule 500 may be defined to function as an exception to a target rule 504, designed to be applied before the target rule 504 to apply what has been learned from observing secondary determinations 312 for that target rule 504. As shown, the first data tag of the first probationary rule 500 is the same as the first data tag of the target rule 504, the result of the first probationary rule 500 is equal to the secondary determination 312a just received. According to various embodiments, at least one of the comparator 202 and the comparison value 204 of the first probationary rule 500 deviates from what is defined in the target rule 504 to create an exception that, when applied to the adjudication request 120a before the application of the target rule 504, the result is the same as the secondary determination 312a.

In some embodiments, a probationary rule 500 may be generated in response to the receipt of any secondary determination 312. In other embodiments, the generation of probationary rules 500, and subsequent refinement, may be reserved for particular types of edge cases. For example, in some embodiments, the process of creating and refining probationary rules 500 may be limited to cases where a final rule 404 is evaluated, in an effort to expand the breadth of the rules library 116, rather than refine its accuracy. In some cases, it may be desired that certain edge cases always be handled by an agent 310, and thus probationary rules 500 may not be desired for situations already existing within defined rules.

The first probationary rule 500 is stored within the storage 114. See circle '5'. According to various embodiments, a probationary rule 500 is the same as any other rule 118 in a rule library 116, except in some embodiments, probationary rules 500 may also comprise a success rate 502. In the context of the present description and the claims that follow, a success rate 502 of a probationary rule 500 is a representation of how well the probationary rule 500 is performing in its current state. The success rate 502 may be a single quantity (e.g. percent of correct results, etc.), or multiple quantities (e.g. number of applications and number of successes, etc.). The success rate 502 will allow the system 100 or an agent of the arbiter to determine if a probationary rule 500 is performing well enough to be put into use.

After storing the first probationary rule 500 in the storage 114, the target rule 504 is updated to have a reference 506 pointing to the first probationary rule 500. See circle '6'. In some embodiments, the reference 506 may point to the location where the first probationary rule 500 is positioned within the storage 114, while in other embodiments, the reference 506 may indicate a unique identifier by which the first probationary rule 500 may be identified within the storage 114.

The system 100 continues to evaluate adjudication requests 120, until a second adjudication request 120b is received and the target rule 504 is applied, resulting in the rules evaluator 102 sending a second escalated request 312b and receiving the subsequent secondary determination 312b. The first probationary rule 500 is applied to the second adjudication request 120b, and the result is compared to the secondary determination 312b, and the success rate 502 is updated. See circle '7'.

If there is a mismatch, refinement is needed. In cases where the first probationary rule 500 is not satisfied, but the secondary determination 312b is the same as the current result 206 of the first probationary rule 500, at least one of the comparator 202 and the comparison value 204 of the first probationary rule 500 is updated such that an adjudication request identical to the second adjudication request 120b would satisfy the first probationary rule 500. See circle '8'.

In cases where the secondary determination 312b does not match the result of applying the first probationary rule 500, the first probationary rule 500 is refined by creating a second probationary rule 508 (circle '9') as an exception to the first probationary rule 500, applying this same process except now the target rule is the first probationary rule 500.

The first probationary rule 500 is finally inserted into the rule library 304, where it will be applied to future adjudication requests 120 (circle '10') in response to at least one of the receipt of a manual approval 510 from an agent 310 and the success rate 502 of the first probationary rule 500 surpassing a predefined threshold 512. In some embodiments, a rules library 116 may comprise the predefined threshold 512 for determining when a probationary rule 500 may be ready for promotion. In other embodiments, the predefined threshold 512 may be defined within the rules evaluator 102 and applied universally.

In some embodiments, the first probationary rule 500 may be inserted into the rules library 116 such that it operates as an exception to the target rule 504, meaning that the target rule 504 is the next logically adjacent rule 402 to the newly inserted rule. In other embodiments, the rules 118 may be defined in a self-contained format, such that order does not matter. In such as case, the insertion of the probationary rule 500 may be accomplished by combining the first probationary rule 500 and the target rule 504, yielding two new rules that do not overlap. As a specific example, in the case shown in FIG. 5, the comparison value 204 of the first probationary rule 500 is [x,y], and the comparison value 204 of the target rule 504 is (a,b). The two rules could be combined to yield a first rule having a comparison value of (a,x),(y,b) with an escalation result, and a second rule having a comparison value of [x,y] with a sigma result.

In some embodiments, probationary rules may also be formed and guided by information beyond secondary determinations 312. For example, in some embodiments, the system 100 may be incorporated into a larger network of systems that deal with the consequences of the determinations made by the adjudication system 100 down the line. By observing those consequences, rules may be further refined. As a specific example, if a prior authorization is granted by the system 100, or if the system 100 indicates that prior authorization is not needed, and later the arbiter denies that claim, the adjudication system 100 can confirm the result of applying the rules 118 using the logs and/or blockchain ledger to appeal that denial. The result of the appeal can then be used to automatically update the rules 118. Such an approach ensures that the set of rules 118 being fed into the rules evaluator 102 reflects the rules 118 in practice, rather than just the rules 118 in theory.

Other embodiments may also create new rules, or modify old rules, based on observed behavior and outcomes, but may do so within a context that is narrower than the embodiments discussed above, with respect to FIG. 5. For example, in some embodiments, upon receiving a secondary determination 312, the system 100 may extract any reasonings or requirements for the provided outcome from the secondary determination 312. If these details fall within certain, predefined parameters while also matching a set of unique criteria, the rules may be modified to match the requirements outlined in the secondary determination 312.

Figure 6:
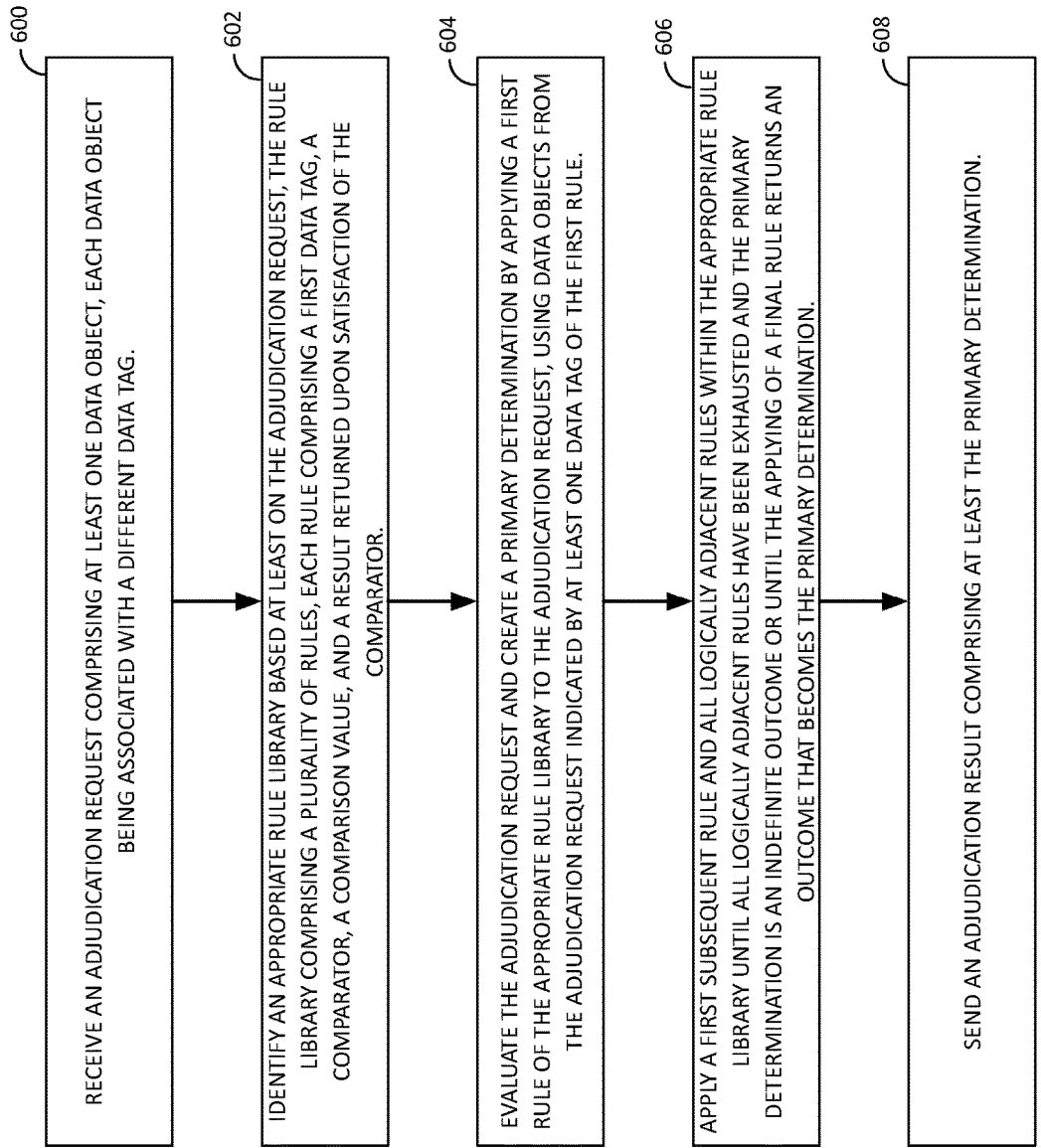
FIG. 6 is a process flow for a method for rules-driven adjudication.

FIG. 6 is a process flow for a non-limiting example of a method for rules-driven adjudication. First, an adjudication request 120 is received through a network interface 110 that is communicatively coupled to a second client 124 through a network 112. See step 600. The adjudication request 120 comprises at least one data object 300, and each data object 300 is associated with a data tag 302. In some embodiments, the adjudication request 120 may be a digital file, while in other embodiments, the adjudication request 120 may be received in the form of a stream that is not a discrete file having a file format recognized by an operating system.

Next, an appropriate rule library 304 is identified and chosen from at least one rule library 116. See step 602. The identification of the appropriate rule library 304 is based, at least in part, on the adjudication request 120. According to various embodiments, each of the at least one rule library 116 comprises a plurality of rules 118, and each rule 118 comprises a first data tag 200, a comparator 202, a comparison value 204, and a result 206, as discussed above. In some embodiments, the comparison value 204 may be one of a second data tag 224 and an external value 210. In some embodiments, the result 206 is one of an outcome 212 and at least one subsequent rules 226. Each outcome 212 is one of a plurality of potential outcomes, which can be definite outcomes and/or indefinite outcomes.

Next, the adjudication request 120 is evaluated and a primary determination is created, by applying a first rule 400 of the appropriate rule library 304 to the adjudication request 120, using data objects from the adjudication request 120 that are indicated by at least one data tag of the first rule 400. See step 604.

After the first rule 400 is applied, a first subsequent rule 226, and all logically adjacent rules 402 within the appropriate rule library 304, are applied until all logically adjacent rules 402 have been exhausted. See step 606. The application of logically adjacent rules 402 continues until the primary determination is an indefinite outcome, or until the applying of a final rule 404 returns an outcome that subsequently becomes the primary determination.

Finally, an adjudication result is sent to the second client 124 through the network interface 110. See step 608. According to various embodiments, the adjudication result comprises at least the primary determination. In some embodiments, it may include an indication of all the rules that were applied, and the result of each application.

The system 100 and method contemplated herein may be applied to a vast range of industries and endeavors. Of particular interest are applications within healthcare management as well as human resources. However, the following exploration of two particular use cases should not be interpreted as limiting.

The healthcare industry is built upon a number of sub-industries that must work together to function, despite sometimes having diverging business interests. For example, providers such as hospitals, laboratories, and pharmacies seek to care for patients while maximizing earnings from those treatments, while payers such as insurers seek to care for patients while minimizing costs. Efforts to minimize disputes have resulted in the prior authorization process (sometimes referred to as pre-authorization, service review, or pre-certification). In the prior authorization process, a payer reviews a proposed expenditure, such as a surgery or a medication ordered by a provider, and decides whether payment for that expenditure would be authorized. Providers benefit from the prior authorization process because it helps them avoid providing services that will not be paid for by insurance, leaving the patient with bills that often are beyond their ability to fully pay. Payers benefit from the prior authorization process because it allows them to review proposed procedures, medications, and other services, and sometimes suggest alternatives that are less expensive for the payer and sometimes the patient.

These benefits are accompanied by a number of drawbacks. Currently, the prior authorization process requires human intervention to process and read through the patient request data. Although many payers offer on-line web portals and APIs that give the impression of an automated system, a human (e.g. a practitioner, etc.) must review each of the requests. It can take many hours, days, or even weeks to get a decision on whether or not the proposed expenditure is authorized. Examples specific to the healthcare industry include, but are not limited to, Availity, Navinet, as well as some custom payer portals.

Additionally, conventional prior authorization systems require a person to fill out a form, which may be an electronic form submitted through a web portal, or even a paper form subsequently faxed to the payer for review. Filling out these forms is another opportunity for human error to result in erroneous responses, leading to later disputes or denial of covered services.

Another problem with conventional prior authorization processes and systems stems from the review being performed by a person. Although payers have defined policies and procedures for determining whether something should be authorized, those policies and procedures can be misinterpreted and are often applied inconsistently. Even worse, human bias, whether subconscious or deliberate, can skew the application of these policies and procedures. Factors such as race, gender, age, even how a person name sounds can sometimes color a reviewers application of the payers policies. All of these human errors can result in the payer later refusing to pay for a procedure that wasn't properly authorized, or prevent a patient from receiving needed care that should have been covered had the policies been properly implemented.

Furthermore, it is difficult for providers and patients to find and understand these policies and procedures established by the payer. They can be sometimes be spread across multiple websites, and easily fall out of date. This can make it difficult for providers and patients to determine whether the authorization adjudication was flawed, or even to plan what request to make of the payer in the first place.

Figure 7:
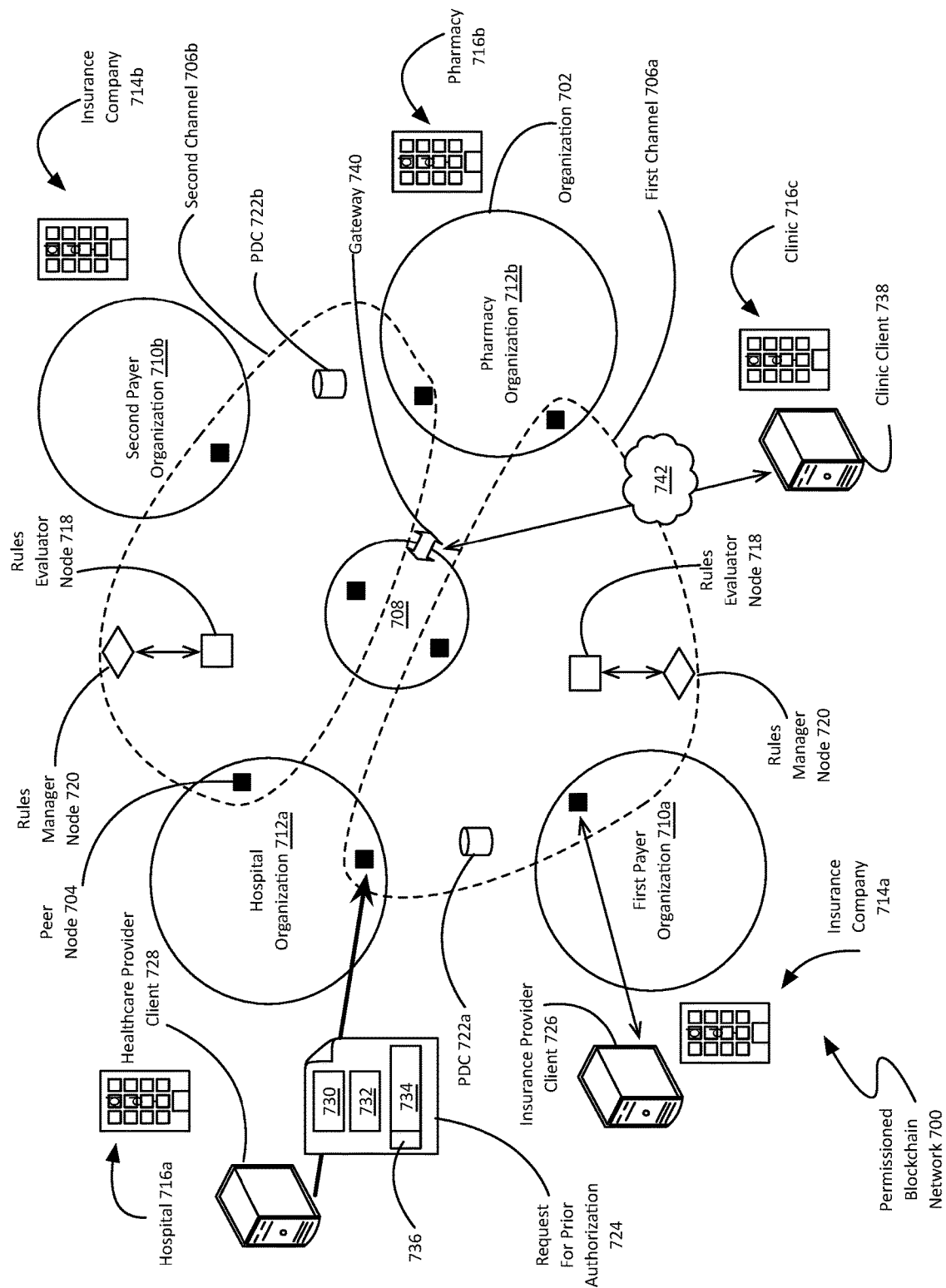
FIG. 7 is a process view of a use case adjudicating prior authorization requests.

FIG. 7 is a network view of a non-limiting example of a rules-driven adjudication system 100 being implemented in a permissioned blockchain network 700 to evaluate prior authorization requests. A payer 710 is able to define a series of rules 118 that codify their policies regarding the circumstances where an expenditure is or is not covered. Once in place, these rules 118 are applied by a rules evaluator 102 to a request for pre-authorization 724, which comprises the information needed to make the determination, providing immediate feedback without the need for any intermediate human intervention. The rules 118 can be implemented and updated quickly by the payer 710, allowing the authorization process to iteratively improve at a much faster pace than is possible in conventional methods, where a workforce has to be trained and retrained on changing authorization policies.

The adjudication system 100 provides many advantages over conventional methods of providing prior authorization. The system can provide a decision regarding prior authorization in a matter of seconds, rather than the hours, days, or even weeks required by conventional methods. Some embodiments of the adjudication system 100 log every step of the evaluation of a request, which may be used to provide a reason for the decision that was rendered that would otherwise be difficult or impossible to get.

The adjudication system 100 is advantageous over conventional prior authorization methods and systems because it applies the rules 118 defined by a payer 710 consistently, and without bias. The policies surrounding what is and is not covered by a particular policy for a particular condition can be complicated, and subject to misinterpretation by the humans that conventional methods rely on. An additional advantage is that, by logging each step of the adjudication process, the adjudication system 100 facilitates oversight of the authorization process, whether by a regulator agency or by the payer itself.

Another advantage provided by the adjudication system 100 is that, by cutting out the use of web portals, paper forms, and fax machines on which conventional methods depend, there is less chance of input errors resulting in erroneous verdicts regarding authorization that can lead to later conflict or ineffective patient care. Some embodiments of the adjudication system 100 can integrate with the EHR/EMR record systems in use by providers 712 and payers 710, ingesting patient information directly from these systems without requiring an individual to transcribe it into a web or paper form.

The vastly improved consistency and speed of the adjudication system 100, when compared to conventional methods and systems, permits the implementation of authorization policies that are much more granular than would have been practical in the past. The rules evaluator 102 can select and apply a rule library 116 in near real-time, even when the rules consider many more factors that would be practical to have a person consider in conventional methods. This improved granularity allows payers 710 to implement rules 118 with built in exceptions for situations that previously would have required additional time and effort on the part of the payer to handle. Some edge cases may still require human intervention; the adjudication system 100 can automatically handle the bulk of the authorization requests, as well as recognize the edge cases and forward them on to a payer agent for consideration.

It should be noted that while the bulk of the discussion about the adjudication system 100 contemplated herein will be done in the context of prior authorization, those skilled in the art will recognize that other healthcare-related queries may also be answered with very little modification. Those other queries include, but are not limited to, the degree of patient responsibility, eligibility, and the like.

As previously mentioned, FIG. 7 is a network view of a non-limiting example of a rules-driven adjudication system 100 being implemented in a permissioned blockchain network 700. Specifically, two instances of a rules-driven adjudication system 100 are being implemented in a permissioned blockchain network 700 that is made up of five organizations 702 (circles) that are members of at least one of two channels 706 (dashed zones). The squares are peer nodes 704. Those skilled in the art will recognize that other nodes are not shown (e.g. an ordering service, orderer nodes, certificate authority nodes, etc.), and are not pertinent to the present discussion, which is an exemplary implementation of a rules-based adjudication system 100 configured for making prior authorization decisions for healthcare payers, within a blockchain network.

As shown, the permissioned blockchain network 700 of FIG. 7 is made up of five organizations 702, or entities that are represented within the blockchain network 700 by one or more permissioned nodes. The five organizations 702 include two insurance companies 714a and 714b (or payers 710) represented by a first payer organization 710a and second payer organization 710b, and two providers 712 (a hospital 716a represented by a hospital organization 712a and a pharmacy 716b represented by a pharmacy organization 712b), and a manager organization 708, who is charged with the maintenance and oversight of the blockchain network 700. It should be noted that, going forward, the blockchain organizations 702 and the entities they represent may be referred to interchangeably.

According to various embodiments, each insurance company 714 defines at least one rule library 116 that is stored within a private data collection 722 within the blockchain network 700. In some embodiments, an insurance company 714 may define a universal rules library 116, for use with all healthcare providers 716 (e.g. a set policy for prior authorization of CAT scans independent of provider, etc.). In some embodiments, a payer 710 may define a rule or rules library 116 for one or more specific providers 716 (e.g. preferred providers may have different prior authorization thresholds, etc.).

In the context of the present description, a rule library 118 is a codification of all of the requirements or parameters from a specific payer that need to be met before prior authorization can be granted for an expenditure (e.g. treatment, service, pharmaceutical, test, etc.). Some rules 118 and rules libraries 116 may be specific to a particular expenditure, like an angiogram through the femoral vein. In some embodiments, some rules 118 may apply to a particular type or class of expenditures, like a rules library 116 defining the parameters for prior authorization for all macrolide antibiotics.

In some embodiments, some or all of the rules within a rule library may rely on one or more codification systems commonly used in healthcare. Examples include, but are not limited to, the Healthcare Common Procedure Coding System (HCPCS), Current Procedural Terminology (CPT), National Drug Code (NDC), International Classification of Diseases (ICD), and the like. Using one or more of these standard coding systems may accelerate the creation of comprehensive rules libraries, further reducing the barrier to participation for smaller entities within the healthcare system and facilitating integration with legacy EMR/EHR systems.

The rules 118 may operate on specific values or attributes (e.g. is patient diabetic?, etc.) as well as ranges or thresholds (e.g. is patient under 65 years old?, is patient over 300 pounds?, etc.), diagnostic testing results, and other data types discussed above. In some embodiments, the rules 118 may operate on information entered in prose, such as narrative description data, and the like.

According to various embodiments, each payer 710 is able to define or update rules 118 using a rules manager node 720, represented as diamonds. In the non-limiting example shown in FIG. 7, each rules evaluator node 718 has an associated rules manager node 720 that is communicatively coupled to the rules evaluator node 718, similar to the non-limiting example shown in FIG. 1. In other embodiments, the rules manager 104 may sit outside the blockchain network 700. The payers 710 may interact with a rules manager node 720 through blockchain transactions in some embodiments, and through a direct interface external to the blockchain in others (e.g. web interface, REST API, etc.).

In some embodiments, each channel 706 may comprise at least one rules manager node 720, or a node (i.e. rules evaluator node 718) that is communicatively coupled to a rules manager 104 that sits outside the channel 706 and the blockchain network 700 (e.g. payer 710 interfaces with the rules manager node 720 through means other than the blockchain such as a web interface). In other embodiments, the rules manager node 720 may exist as a node within the manager 708, which bridges all channels 706.

According to various embodiments, rules that are defined or modified through a rules manager node 720 are added to the blockchain network 700 as an endorsed proposed ledger transaction, eventually ending up in a private data collection 722 (hereinafter PDC 722), which operates as the storage of FIG. 1. According to various embodiments, each rule 118 has an ID code or index with which it is stored in the PDC 722, and by which it is referred to in the blockchain ledger, for brevity and privacy. Rule libraries 116 may be similarly defined and stored, according to various embodiments.

As shown, the non-limiting example of a permissioned blockchain network 700 in FIG. 7 has two channels 706a and 706b. The use of channels 706 in conjunction with the rules-driven adjudication system 100 is advantageous because channels 706 provide a private network available to some organizations 702 and shielded from the rest. The organizations 702 within a channel 706 have a shared ledger with all transactions, and shared access to the PDC 722. This means that the rules 118 stored in the PDC 722 of that channel 706 are scoped to the participants of that channel 706. In the example shown in FIG. 7, each channel 706 has a single payer 710 and two providers 712. Such a partitioning would prevent first payer organization 710a from having access through the blockchain to the rules defined by first payer organization 710b, because those rules are stored in the second PDC 722b that is only available to peers in the second channel 706b.

In some embodiments, each payer 710 may shield their rules from other payers 710 or other organizations 702. In other embodiments, limited access may be provided to rules 118 (e.g. read but not write access, etc.), which may serve to provide greater transparency to decisions, as well as drive competition.

In some embodiments, a channel 706 may have more than one rules evaluator node 718. For example, if the volume of prior authorization requests 724 rises above a defined level, or a performance metric degrades beyond a certain point, additional rules evaluator nodes 718 may be instantiated (similar to what is done with orderer nodes and peer nodes). Depending on how the channel access permissions are defined, one rules evaluator node 718 may have different rules libraries 116 available to it than another rules evaluator node 718.

FIG. 7 also shows another provider entity, a clinic 716c, that is not a participant in the permissioned blockchain network 700. According to various embodiments, the blockchain network 700 may have an interface or gateway 740 through which external systems may submit requests, through a network 742, intended for organizations 702 within the blockchain network 700. Said interface may also serve to transform an incoming data object into a format that is compatible with the blockchain network 700 operations. Having a defined, universal schema streamlines the operations within the blockchain network 700, as each node will know what to expect. Blockchain participants may submit an adjudication request 120 directly to the blockchain for automatic, near real-time evaluation.

The process for submitting an adjudication request 120, which here is a request for prior authorization 724, is similar to the process discussed above, outside a blockchain network 700. A healthcare provider client 728 (i.e. the second client 122) submits the request for prior authorization 724 to a peer node 704 within the organization 702 that represents said healthcare provider 716 within the blockchain network 700. In this case, a peer node 704 in the hospital organization 712a.

According to various embodiments, the request for prior authorization 724 comprises a plurality of data objects 300 of various types, including patient information 730, insurance policy information 732, and treatment information 734. The patient information 730 includes data that is known to be, or potentially may be, pertinent to determining prior authorization. This information may include, but is not limited to, name, age, weight, height, ailment, address, medical history, lab results, and the like. In some embodiments, the patient information 730 is provided to the rules evaluator node 718 in a predefined schema, while in other embodiments, the request for prior authorization 724 may be transformed to meet the requirements of a predefined schema, allowing the rules evaluator node 718 to understand and operate upon input from various EMR/EHR systems having various data formats. As an option, said transformation may be performed by the evaluator itself, in some embodiments.

According to various embodiments, the policy information 732 may include, but is not limited to, a policy number, a policy name, primary insurance provider, secondary insurance provider, and the like. Furthermore, the treatment information 734 may include, but is not limited to, a proposed treatment, a provider, and the like. The treatment information 734 may further include at least one medical code 736. In some embodiments, the treatments and ailments may be codified within the rules 118 using systems such as the Healthcare Common Procedure Coding System (HCPCS), the International Classification of Diseases (ICD), and the like. In other embodiments, the rules 118 may identify the pertinent expenditure and/or ailment using more than one method, including but not limited to a code, a common name, a brand name, a generic name, a chemical formula, and the like.

When an adjudication request 120 has been placed into the blockchain network 700, chain code (or a smart contract) for that type of request will determine if the needed payer 710 is a participant of the blockchain network 700. If the desired payer 710 is a participant, the adjudication request 120 is sent to a rules evaluator node 718 that has permission to access rules libraries 116 associated with that particular payer 710 and the source provider 712. If the desired payer 710 is not on the blockchain network 700 (or if a definitive answer is not possible), the request may proceed through a separate path of execution. In some embodiments, this may comprise interfacing with the conventional prior authorization systems mentioned previously.

Once the proper rules library 116 has been found by the rules evaluator, the library 116 is applied to the request for prior authorization 724, as described above. According to various embodiments, the rules evaluator node 718 may come to one of two definite outcomes: "yes" (i.e. proposed expenditure authorized), or "no" (i.e. proposed expenditure will not be paid by payer), or potentially one of two indefinite outcomes: "needs further consideration" or "unable to evaluate request". In other embodiments, the response may be framed as one of two definite outcomes: "no prior authorization needed" (i.e. proceed, payer will cover it) and "prior authorization needed" (i.e. it's a no but a human needs to take a look just in case, it is an edge case, etc.).

According to various embodiments, each step of the rules library 116 identification and evaluation process is added to the blockchain ledger as transactions, providing a detailed log for the other participants to see and verify. The operation of the rules-driven adjudication system 100 within a permissioned blockchain is advantageous over conventional methods and systems because the immutable ledger provides an auditable log that is beneficial from a regulatory point of view. The immutability of the ledger also keeps all parties honest, and can be used to quickly resolve disputes that are a common occurrence within conventional prior authorization systems and workflows.

Having each step of the rules-based adjudication process logged in the ledger also assists in the development of new rules 318 and/or the refinement of existing rules 118. The ledger will contain the stages of the rule application process, the result, and subsequent events such as denial by the payer 710 or appeal by the provider 712 or patient. Those outcomes can be used to improve a rule library 116 and potentially reduce the number of future problems.

As mentioned, in some embodiments, the end result of the revenue cycle (e.g. payer 710 covered the expense, payer 710 denied expense, etc.) can be used to improve a rule library 116. As previously discussed, in some embodiments, this data combined with patient data and rule data may be used to create a model to automatically suggest new or modified rules that are more effective for all parties involved. As an option, the result data may also include the degree to which the procedure, medication, etc. was successful, allowing a model to balance cost with efficacy. Such a model may also assist a payer 710 in defining rules that would prefer one treatment or medication over another, and would be based on results of the rules and medicine as applied, rather than in theory. As an option, the data may be programmatically scrubbed of sensitive data before modeling, to stay in compliance with regulations concerning the privacy of healthcare records and personally identifying information.

Policies governing employee conduct, performance, and discipline are a standard part of a human resources department. However, the codification of these policies, and the consistent enforcement of these policies are two very different affairs, particularly in large organizations. The consistent application of rules and policies to employees, particularly employees that are "similarly situated" is crucial, not only to maintain a healthy and loyal relationship with employees, but to also avoid legal claims from employees who have been treated unfairly.

The contemplated system 100 and methods for adjudication of rules is advantageous over conventional methods for ascertaining compliance with HR policy for a number of reasons. They are able to consistently apply even a complicated set of rules that might get glossed over by a supervisor when considering taking an action. Additionally, the adjudication system 100 can make a determination by taking into account every pertinent detail about an employee, much more information than any single supervisor would be able to ingest and accurately recall. Furthermore, the adjudication system 100 is able to apply the defined rules consistently, without any bias, and can do so in near real-time. Also, the adjudication system 100 is able to operate over an entire organization, across departmental boundaries, ensuring that there are no patterns of behavior that deviate from the desired norms, even if the patterns cross departmental boundaries, making them hard to detect by any single department, but visible when taken as a whole.

Figure 8:
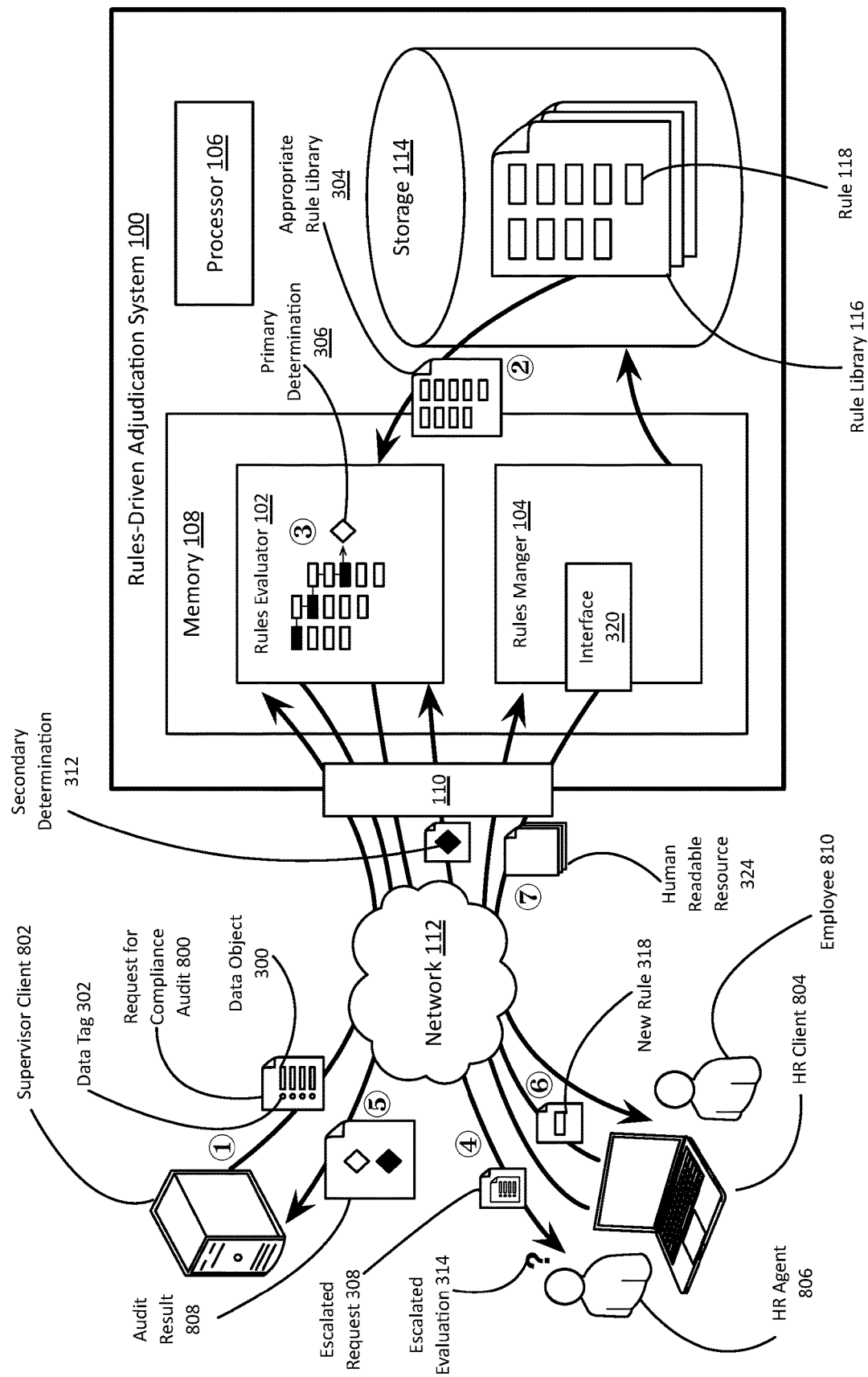
FIG. 8 is a process view of a use case adjudicating HR policy.

FIG. 8 is a process view of a non-limiting example of a rules-driven adjudication system 100 applied to the adjudication of HR policy. Specifically, a determination if a particular action, such as a disciplinary action, conforms with established human resources policies. As shown, an adjudication request 120, here a request for compliance auditing 800, is received by the rules evaluator 102 through the network interface 110 from a supervisor client 802. See circle '1'. A supervisor client 802 is a computing device operated by and authenticated to the supervisor requesting the compliance check for a particular action. According to various embodiments, the request for compliance auditing 800 comprises the information that will be needed to perform the compliance check, such as information stored as at least one data object 300, each data object 300 having an associated data tag 302. Additionally, in some embodiments, the request for compliance auditing 800 also indicates the desired determination, when a rules evaluator 102 is configured to execute more than one type of adjudication, whether by having access to more than one rule library 116, or through a rule library 116 that is constructed for use in more than one type of adjudication (e.g. determining candidates for promotion, hiring, etc.).

Since the adjudication system 100 is being implemented within the same organization originating the request, most of the information about the employee is already available. Such information may include, but is not limited to, employment history, performance reviews, resume, application materials, training, background checks, certifications, incident reports, evaluations, medical reports, and the like. Unlike other use cases discussed above, in this specific example, the request for compliance auditing 800 may simply provide a unique identifier for the employee, such as an ID number, and indicate the nature and specifics of the proposed action.

Next, the rules evaluator 102 identifies an appropriate rule library 304 from the one or more rule libraries 116 stored in the storage 114. See circle '2'. In some embodiments, an appropriate rules library 304 may be identified by matching a predetermined data object 300 within the request for compliance auditing 800 that, due to the nature of requests being made of the system 100, is indicative of a specific group of rules 118. As a specific example, in an embodiment used to evaluate if decisions are in compliance with human resource policies, the appropriate rule library 304 may be chosen based upon the particular department where the employee works, rather than the department making the request.

Next, the rules evaluator 102 evaluates the request for compliance auditing 800 and creates a primary determination 306. See circle '3'. The primary determination 306 (i.e. the white diamond in FIG. 8) is the outcome 212 that is the result of the rules evaluator 102 applying a rules library 116 to the request for compliance auditing 800. In the case of the rules evaluator 102 running out of rules 118 to apply, or otherwise not being able to make the determination requested, the primary determination 306 will be an indefinite outcome 222. As previously stated, in some embodiments, upon the arrival at an indefinite outcome 222, the rules evaluator 102 may return the indefinite outcome 222 to the supervisor client 124 as an audit result 316, informing the requestor that another method should be used.

In other embodiments, including the non-limiting example of FIG. 8, if the rules evaluator 102 arrives at a primary determination 306 having an indefinite outcome 222, or an indefinite outcome 222 that explicitly requests escalation, an escalated request 308 is sent to a HR client 804 that is communicatively coupled to the rules evaluator 102. See circle '4'. According to various embodiments, the escalated request 308 comprises at least the request for compliance auditing 800. In some embodiments, the escalated request 308 may also include a log of the various rules 118 applied by the rules evaluator 102, and the results of each application, that culminated in the arrival at an indefinite outcome 222.

A HR client 804 is a computing device operated by and authenticated to an agent 806 of the HR department. In this case, the HR client 804 is operated by a HR agent 806, who receives and evaluates the escalated request 308. In the context of the present description and the claims that follow, a HR agent 806 is an individual authorized to make determinations like the determination being requested of the system 100.

The HR agent 806 makes an evaluation of the escalated request 308, and sends, through the HR client 804, a secondary determination 312 indicating the result of the evaluation 314 back to the rules evaluator 102. Then, the rules evaluator 102 sends an audit result 808 back to the supervisor client 802 through the network interface 110. See circle '5'. According to various embodiments, the audit result 808 comprises at least a primary determination 306. In embodiments that make use of escalated requests 308, the adjudication result 316 may contain the secondary determination 312.

In some embodiments, the audit result 808 may also comprise a log of the rules applied, and their results, giving a level of transparency to the audit not typically found in conventional systems and methods. As shown, the adjudication system 100 also comprises a rules manager 104 through which an HR agent 806 may define a new rule 318, update a rule 118 or a rules library 116. See circle '6'. In some embodiments, the HR agent 806 may interact with the rules manager 104 through the HR client 804, using any method known in the art, including but not limited to an API, a web interface, an application, and the like. Once a new rule 318 has been defined by the HR agent 806, and received and stored within a rules library 116 by the rules manager 104, no further human interaction is needed.

As previously mentioned, an additional advantage to storing the rules 118 in a human-readable format 208 is that the rules library 116 may be used as a reference. According to various embodiments, the rules manager 104 is further configured to provide, through the network interface 110, an interface 320 in which at least one rule library 116 is formatted and through which the at least one rule library 116 is made available to an employee 810 as a human readable resource 324. See circle '7'.

The process for automatically developing new or modified rules, as discussed with respect to FIG. 5, has a different purpose with respect to compliance with HR policy. The policies codified within the rules library 116 are not intended to change, but rather represent the ideal that the company is striving to live up to. However, the rules evaluator 102, by monitoring the decisions made by the HR agents 806, or the ultimate decision made by the supervisor after performing the audit, will begin to develop probationary rules, as previously discussed. According to various embodiments, the system 100 may be configured to, once a threshold success rate has been achieved (most likely much lower than in the embodiments used to create new rules for application), the probationary rule is examined to see what information it is using to match the actual actions taken. If it is found that the probationary rule is conditioned on aspects such as gender, race, or similar information, an alarm is raised with the HR department, and the pattern is examined in greater detail. Such as system 100 is advantageous over conventional oversight systems, as it can account for actions taken across departments, even in a large company, and detect patterns of different treatment of similarly situated employees much earlier than would be possible otherwise.

Figure 9:
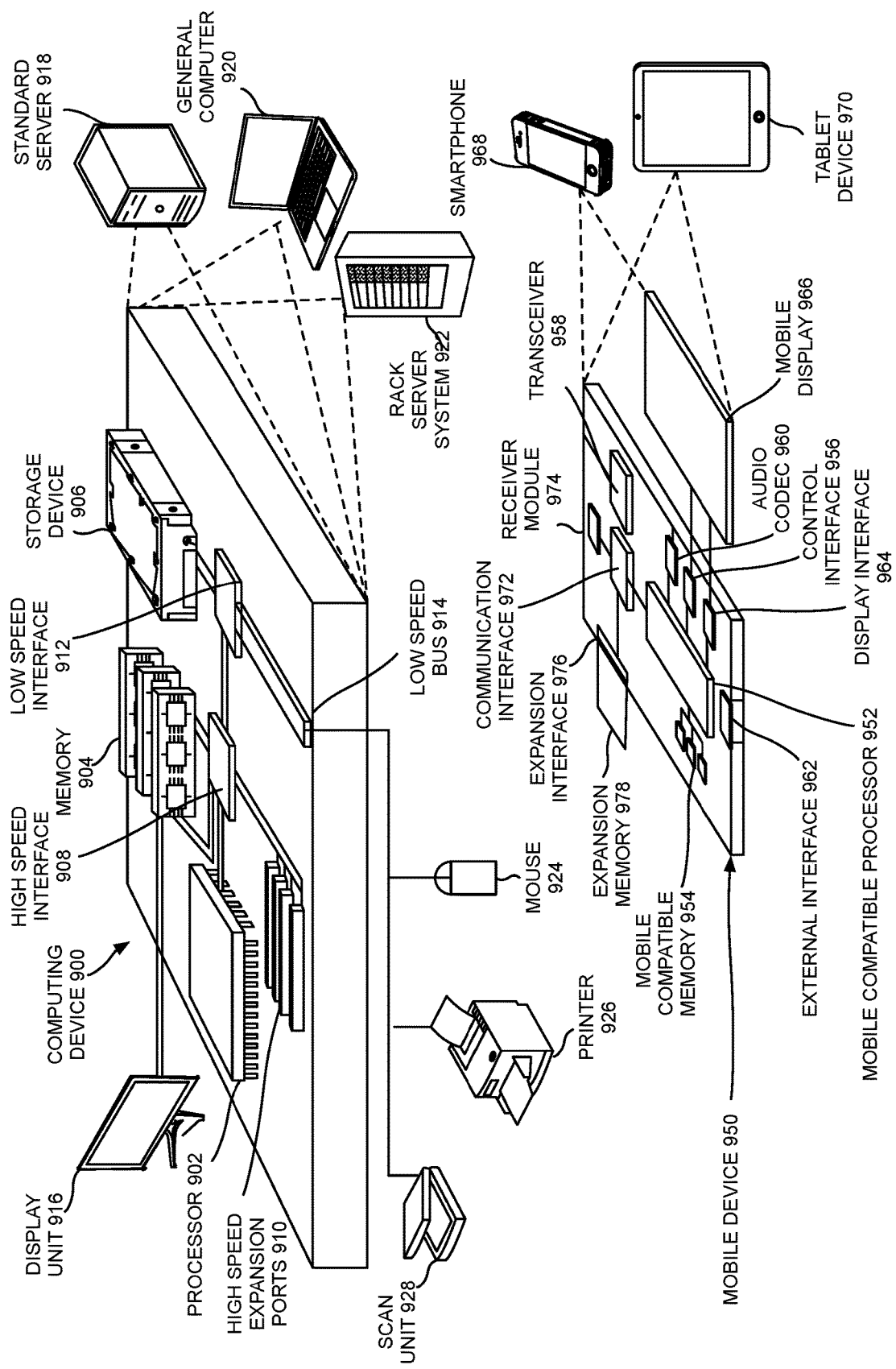
FIG. 9 is a schematic view of a specific computing device that can be used to implement the methods and systems disclosed herein, according to one or more embodiments.

FIG. 9 is a schematic diagram of specific computing device 900 and a specific mobile computing device 950 that can be used to perform and/or implement any of the embodiments disclosed herein. According to various embodiments, the rules-driven adjudication system 100, the rules evaluator 102, the rules manager 104, the first client 122, and/or the second client 124 of FIG. 1, also the peer node 704, the rules evaluator node 718, the rules manager node 720, the private data collection 722, the insurance provider client 726, and/or the medical provider client 728 of FIG. 7, and supervisor client 802 and/or HR client 804 of FIG. 8 may be the specific computing device 900.

The specific computing device 900 may represent various forms of digital computers, such as laptops, desktops, workstations, personal digital assistants, servers, blade servers, mainframes, and/or other appropriate computers. The specific mobile computing device 950 may represent various forms of mobile devices, such as smartphones, camera phones, personal digital assistants, cellular telephones, and other similar mobile devices. The components shown here, their connections, couples, and relationships, and their functions, are meant to be exemplary only, and are not meant to limit the embodiments described and/or claimed, according to one embodiment.

The specific computing device 900 may include a processor 902, a memory 904, a storage device 906, a high speed interface 908 coupled to the memory 904 and a plurality of high speed expansion ports 910, and a low speed interface 912 coupled to a low speed bus 914 and a storage device 906. In one embodiment, each of the components heretofore may be inter-coupled using various buses, and may be mounted on a common motherboard and/or in other manners as appropriate. The processor 902 may process instructions for execution in the specific computing device 900, including instructions stored in the memory 904 and/or on the storage device 906 to display a graphical information for a GUI on an external input/output device, such as a display unit 916 coupled to the high speed interface 908, according to one embodiment.

In other embodiments, multiple processors and/or multiple buses may be used, as appropriate, along with multiple memories and/or types of memory. Also, a plurality of specific computing device 900 may be coupled with, with each device providing portions of the necessary operations (e.g., as a server bank, a group of blade servers, and/or a multi-processor system).

The memory 904 may be coupled to the specific computing device 900. In one embodiment, the memory 904 may be a volatile memory. In another embodiment, the memory 904 may be a non-volatile memory. The memory 904 may also be another form of computer-readable medium, such as a magnetic and/or an optical disk. The storage device 906 may be capable of providing mass storage for the specific computing device 900. In one embodiment, the storage device 906 may be includes a floppy disk device, a hard disk device, an optical disk device, a tape device, a flash memory and/or other similar solid state memory device. In another embodiment, the storage device 906 may be an array of the devices in a computer-readable medium previously mentioned heretofore, computer-readable medium, such as, and/or an array of devices, including devices in a storage area network and/or other configurations.

A computer program may be comprised of instructions that, when executed, perform one or more methods, such as those described above. The instructions may be stored in the memory 904, the storage device 906, a memory coupled to the processor 902, and/or a propagated signal.

The high speed interface 908 may manage bandwidth-intensive operations for the specific computing device 900, while the low speed interface 912 may manage lower bandwidth-intensive operations. Such allocation of functions is exemplary only. In one embodiment, the high speed interface 908 may be coupled to the memory 904, the display unit 916 (e.g., through a graphics processor and/or an accelerator), and to the plurality of high speed expansion ports 910, which may accept various expansion cards.

In the embodiment, the low speed interface 912 may be coupled to the storage device 906 and the low speed bus 914. The low speed bus 914 may be comprised of a wired and/or wireless communication port (e.g., a Universal Serial Bus ("USB"), a Bluetooth® port, an Ethernet port, and/or a wireless Ethernet port). The low speed bus 914 may also be coupled to the scan unit 928, a printer 926, a keyboard, a mouse 924, and a networking device (e.g., a switch and/or a router) through a network adapter.

The specific computing device 900 may be implemented in a number of different forms, as shown in the figure. In one embodiment, the specific computing device 900 may be implemented as a standard server 918 and/or a group of such servers. In another embodiment, the specific computing device 900 may be implemented as part of a rack server system 922. In yet another embodiment, the specific computing device 900 may be implemented as a general computer 920 such as a laptop or desktop computer. Alternatively, a component from the specific computing device 900 may be combined with another component in a specific mobile computing device 950. In one or more embodiments, an entire system may be made up of a plurality of specific computing device 900 and/or a plurality of specific computing device 900 coupled to a plurality of specific mobile computing device 950.

In one embodiment, the specific mobile computing device 950 may include a mobile compatible processor 952, a mobile compatible memory 954, and an input/output device such as a mobile display 966, a communication interface 972, and a transceiver 958, among other components. The specific mobile computing device 950 may also be provided with a storage device, such as a microdrive or other device, to provide additional storage. In one embodiment, the components indicated heretofore are inter-coupled using various buses, and several of the components may be mounted on a common motherboard.

The mobile compatible processor 952 may execute instructions in the specific mobile computing device 950, including instructions stored in the mobile compatible memory 954. The mobile compatible processor 952 may be implemented as a chipset of chips that include separate and multiple analog and digital processors. The mobile compatible processor 952 may provide, for example, for coordination of the other components of the specific mobile computing device 950, such as control of user interfaces, applications run by the specific mobile computing device 950, and wireless communication by the specific mobile computing device 950.

The mobile compatible processor 952 may communicate with a user through the control interface 956 and the display interface 964 coupled to a mobile display 966. In one embodiment, the mobile display 966 may be a Thin-Film-Transistor Liquid Crystal Display ("TFT LCD"), an Organic Light Emitting Diode ("OLED") display, and another appropriate display technology. The display interface 964 may comprise appropriate circuitry for driving the mobile display 966 to present graphical and other information to a user. The control interface 956 may receive commands from a user and convert them for submission to the mobile compatible processor 952.

In addition, an external interface 962 may be provide in communication with the mobile compatible processor 952, so as to enable near area communication of the specific mobile computing device 950 with other devices. External interface 962 may provide, for example, for wired communication in some embodiments, or for wireless communication in other embodiments, and multiple interfaces may also be used.

The mobile compatible memory 954 may be coupled to the specific mobile computing device 950. The mobile compatible memory 954 may be implemented as a volatile memory and a non-volatile memory. The expansion memory 978 may also be coupled to the specific mobile computing device 950 through the expansion interface 976, which may comprise, for example, a Single In Line Memory Module ("SIMM") card interface. The expansion memory 978 may provide extra storage space for the specific mobile computing device 950, or may also store an application or other information for the specific mobile computing device 950.

Specifically, the expansion memory 978 may comprise instructions to carry out the processes described above. The expansion memory 978 may also comprise secure information. For example, the expansion memory 978 may be provided as a security module for the specific mobile computing device 950, and may be programmed with instructions that permit secure use of the specific mobile computing device 950. In addition, a secure application may be provided on the SIMM card, along with additional information, such as placing identifying information on the SIMM card in a non-hackable manner.

The mobile compatible memory may include a volatile memory (e.g., a flash memory) and a non-volatile memory (e.g., a non-volatile random-access memory ("NVRAM")). In one embodiment, a computer program comprises a set of instructions that, when executed, perform one or more methods. The set of instructions may be stored on the mobile compatible memory 954, the expansion memory 978, a memory coupled to the mobile compatible processor 952, and a propagated signal that may be received, for example, over the transceiver 958 and/or the external interface 962.

The specific mobile computing device 950 may communicate wirelessly through the communication interface 972, which may be comprised of a digital signal processing circuitry. The communication interface 972 may provide for communications using various modes and/or protocols, such as, a Global System for Mobile Communications ("GSM") protocol, a Short Message Service ("SMS") protocol, an Enhanced Messaging System ("EMS") protocol, a Multimedia Messaging Service ("MMS") protocol, a Code Division Multiple Access ("CDMA") protocol, Time Division Multiple Access ("TDMA") protocol, a Personal Digital Cellular ("PDC") protocol, a Wideband Code Division Multiple Access ("WCDMA") protocol, a CDMA2000 protocol, and a General Packet Radio Service ("GPRS") protocol.

Such communication may occur, for example, through the transceiver 958 (e.g., radio-frequency transceiver). In addition, short-range communication may occur, such as using a Bluetooth®, Wi-Fi, and/or other such transceiver. In addition, a GPS ("Global Positioning System") receiver module 974 may provide additional navigation-related and location-related wireless data to the specific mobile computing device 950, which may be used as appropriate by a software application running on the specific mobile computing device 950.

The specific mobile computing device 950 may also communicate audibly using an audio codec 960, which may receive spoken information from a user and convert it to usable digital information. The audio codec 960 may likewise generate audible sound for a user, such as through a speaker (e.g., in a handset smartphone of the specific mobile computing device 950). Such sound may comprise a sound from a voice telephone call, a recorded sound (e.g., a voice message, a music files, etc.) and may also include a sound generated by an application operating on the specific mobile computing device 950.

The specific mobile computing device 950 may be implemented in a number of different forms, as shown in the figure. In one embodiment, the specific mobile computing device 950 may be implemented as a smartphone 968. In another embodiment, the specific mobile computing device 950 may be implemented as a personal digital assistant ("PDA"). In yet another embodiment, the specific mobile computing device, 950 may be implemented as a tablet device 970.

Various embodiments of the systems and techniques described here can be realized in a digital electronic circuitry, an integrated circuitry, a specially designed application specific integrated circuits ("ASICs"), a piece of computer hardware, a firmware, a software application, and a combination thereof. These various embodiments can include embodiment in one or more computer programs that are executable and/or interpretable on a programmable system including one programmable processor, which may be special or general purpose, coupled to receive data and instructions from, and to transmit data and instructions to, a storage system, one input device, and at least one output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here may be implemented on a computing device having a display device (e.g., a cathode ray tube ("CRT") and/or liquid crystal ("LCD") monitor) for displaying information to the user and a keyboard and a mouse by which the user can provide input to the computer. Other kinds of devices can be used to provide for interaction with a user as well; for example, feedback provided to the user can be any form of sensory feedback (e.g., visual feedback, auditory feedback, and/or tactile feedback) and input from the user can be received in any form, including acoustic, speech, and/or tactile input.

The systems and techniques described here may be implemented in a computing system that includes a back end component (e.g., as a data server), a middleware component (e.g., an application server), a front end component (e.g., a client computer having a graphical user interface, and/or a Web browser through which a user can interact with an embodiment of the systems and techniques described here), and a combination thereof. The components of the system may also be coupled through a communication network.

The communication network may include a local area network ("LAN") and a wide area network ("WAN") (e.g., the Internet). The computing system can include a client and a server. In one embodiment, the client and the server are remote from each other and interact through the communication network.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

Where the above examples, embodiments and implementations reference examples, it should be understood by those of ordinary skill in the art that other use case, execution environments, and data structures could be intermixed or substituted with those provided. In places where the description above refers to particular embodiments of systems and methods for rule-based adjudication, it should be readily apparent that a number of modifications may be made without departing from the spirit thereof and that these embodiments and implementations may be applied to other systems and methods for adjudication as well. Accordingly, the disclosed subject matter is intended to embrace all such alterations, modifications and variations that fall within the spirit and scope of the disclosure and the knowledge of one of ordinary skill in the art.

What is claimed is:

1. A system for rules-driven adjudication, comprising:
   a processor communicatively coupled to a memory and a network interface, the network interface communicatively coupled to a network;
   a storage comprising at least one rule library, each of the at least one rule library comprising a plurality of rules, each rule of the plurality of rules being in a human-readable format and comprising a first data tag, a comparator, a comparison value, and a result returned upon satisfaction of the comparator, wherein the comparison value is one of a second data tag and an external value and wherein the result is one of an outcome and at least one subsequent rule, each outcome being one of a plurality of potential outcomes comprising at least one definite outcome and at least one indefinite outcome;
   a rules manager configured to receive a new rule through the network interface from a first client, and store the new rule in one of the at least one rule library; and
   a rules evaluator configured to:
      receive an adjudication request through the network interface from a second client, the adjudication request comprising at least one data object, each of the at least one data object being associated with a different data tag;

identify an appropriate rule library from among the at least one rule library to apply based at least on the adjudication request;

evaluate the adjudication request and create a primary determination by applying a first rule of the appropriate rule library to the adjudication request, using data objects from the adjudication request indicated by at least one data tag of the first rule, and further applying a first subsequent rule of the at least one subsequent rules and all logically adjacent rules within the appropriate rule library until all logically adjacent rules have been exhausted and the primary determination is an indefinite outcome or the applying of a final rule returns an outcome that becomes the primary determination;

send, for primary determinations having an indefinite outcome, an escalated request to the first client communicatively coupled to the rules evaluator, the escalated request comprising at least the adjudication request;

receive a secondary determination from the first client, the secondary determination indicating the result of an evaluation of the escalated request performed by a first agent;

send an adjudication result to the second client through the network interface in response to one of the primary determination having a definite outcome and the receipt of the secondary determination, the adjudication result comprising one of the primary determination and the secondary determination;

create a first probationary rule in response to the receipt of the secondary determination by the rules evaluator, the first probationary rule to function as an exception to a target rule that is the final rule, wherein the first data tag of the first probationary rule is the same as the first data tag of the target rule, the result of the first probationary rule is equal to the secondary determination, and wherein at least one of the comparator and the comparison value of the first probationary rule deviates from what is defined in the target rule to create an exception that, when applied to the adjudication request before the application of the target rule, the result is the same as the secondary determination;

store the first probationary rule within the storage, the first probationary rule further comprising a success rate;

add to the target rule a reference pointing to the first probationary rule within the storage;

apply the first probationary rule to another adjudication request resulting in the application of the target rule and the sending of another escalated request;

compare the secondary determination received in response to the another escalated request with the result of the application of the first probationary rule to the another adjudication request, and update the success rate of the first probationary rule;

refine the first probationary rule by one of modifying at least one of the comparator and the comparison value of the first probationary rule and creating a second probationary rule as an exception to the first probationary rule, in response to the first probationary rule's failure to match the secondary determination received in response to the another escalated request; and insert the first probationary rule into the appropriate rule library in response to at least one of the receipt of a manual approval and the success rate of the first probationary rule surpassing a predefined threshold;

wherein the external value is obtained outside of the adjudication request.

2. The system of claim 1:
wherein the adjudication request is a request for prior authorization and comprises patient information, policy information, and treatment information comprising a medical code;
wherein the first client is an insurance provider client;
wherein the second client is a healthcare provider client;
wherein the at least one definite outcome comprises an approval, a denial, and an indication that prior authorization is not required; and
wherein the at least one indefinite outcome comprises an indication that the system in unable to evaluate the request.

3. The system of claim 1, wherein the rules manager is further configured to provide, through the network interface, an interface in which at least one rule library is formatted and through which the at least one rule library is made available to a user as a human readable resource.

4. The system of claim 1, wherein at least one of the first data tag and the second data tag of at least one rule in the appropriate rule library is associated with a derived data object missing from the adjudication request and defined by an expression comprising one or more operations performed on at least one data object of the adjudication request, and wherein the plurality of rules are stored in a JSON format.

5. A system for rules-driven adjudication, comprising:
a processor communicatively coupled to a memory and a network interface, the network interface communicatively coupled to a network;
a storage comprising at least one rule library, each of the at least one rule library comprising a plurality of rules, each rule of the plurality of rules being in a human-readable format and comprising a first data tag, a comparator, a comparison value, and a result returned upon satisfaction of the comparator, wherein the comparison value is one of a second data tag and an external value and wherein the result is one of an outcome and at least one subsequent rule, each outcome being one of a plurality of potential outcomes comprising at least one definite outcome and at least one indefinite outcome;
a rules manager configured to receive a new rule through the network interface from a first client, and store the new rule in one of the at least one rule library; and
a rules evaluator configured to:
receive an adjudication request through the network interface from a second client, the adjudication request comprising at least one data object, each of the at least one data object being associated with a different data tag;
identify an appropriate rule library from among the at least one rule library to apply based at least on the adjudication request;
evaluate the adjudication request and create a primary determination by applying a first rule of the appropriate rule library to the adjudication request, using data objects from the adjudication request indicated by at least one data tag of the first rule, and further applying a first subsequent rule of the at least one subsequent rules and all logically adjacent rules within the appropriate rule library until all logically adjacent rules have been exhausted and the primary determination is an indefinite outcome or the applying of a final rule returns an outcome that becomes the primary determination; and send an adjudication result to the second client through the network interface comprising at least the primary determination;

wherein the external value is obtained outside of the adjudication request.

6. The system of claim 5, wherein the rules evaluator is further configured to:

send, for primary determinations having an indefinite outcome, an escalated request to the first client communicatively coupled to the rules evaluator, the escalated request comprising at least the adjudication request; and receive a secondary determination from the first client, the secondary determination indicating the result of an evaluation of the escalated request performed by a first agent;

wherein the adjudication result is sent to the second client in response to one of the primary determination having a definite outcome and the receipt of the secondary determination, the adjudication result comprising one of the primary determination and the secondary determination.

7. The system of claim 6, wherein the adjudication result sent in response to the receipt of a secondary determination comprises the primary determination and the secondary determination.

8. The system of claim 6, the rules evaluator further configured to:

create a first probationary rule in response to the receipt of the secondary determination by the rules evaluator, the first probationary rule to function as an exception to a target rule, wherein the first data tag of the first probationary rule is the same as the first data tag of the target rule, the result of the first probationary rule is equal to the secondary determination, and wherein at least one of the comparator and the comparison value of the first probationary rule deviates from what is defined in the target rule to create an exception that, when applied to the adjudication request before the application of the target rule, the result is the same as the secondary determination;

store the first probationary rule within the storage, the first probationary rule further comprising a success rate;

add to the target rule a reference pointing to the first probationary rule within the storage;

apply the first probationary rule to another adjudication request resulting in the application of the target rule and the sending of another escalated request;

compare the secondary determination received in response to the another escalated request with the result of the application of the first probationary rule to the another adjudication request, and update the success rate of the first probationary rule;

refine the first probationary rule by one of modifying at least one of the comparator and the comparison value of the first probationary rule and creating a second probationary rule as an exception to the first probationary rule, in response to the first probationary rule's failure to match the secondary determination received in response to the another escalated request; and insert the first probationary rule into the appropriate rule library in response to at least one of the receipt of a manual approval and the success rate of the first probationary rule surpassing a predefined threshold.

9. The system of claim 5:

wherein the adjudication request is a request for prior authorization and comprises patient information, policy information, and treatment information comprising a medical code;

wherein the first client is an insurance provider client;

wherein the second client is a healthcare provider client;

wherein the at least one definite outcome comprises an approval, a denial, and an indication that prior authorization is not required; and wherein the at least one indefinite outcome comprises an indication that the system in unable to evaluate the request.

10. The system of claim 5, wherein the rules manager is further configured to provide, through the network interface, an interface in which at least one rule library is formatted and through which the at least one rule library is made available to a user as a human readable resource.

11. The system of claim 5, wherein at least one of the first data tag and the second data tag of at least one rule in the appropriate rule library is associated with a derived data object missing from the adjudication request and defined by an expression comprising one or more operations performed on at least one data object of the adjudication request.

12. A method for rules-driven adjudication, comprising:

receiving an adjudication request through a network interface communicatively coupled to a second client through a network, the adjudication request comprising at least one data object, each of the at least one data object being associated with a different data tag;

identifying an appropriate rule library from at least one rule library to apply, the identification based at least on the adjudication request, wherein each of the at least one rule library comprises a plurality of rules, each rule of the plurality of rules comprising a first data tag, a comparator, a comparison value, and a result returned upon satisfaction of the comparator, wherein the comparison value is one of a second data tag and an external value and wherein the result is one of an outcome and at least one subsequent rule, each outcome being one of a plurality of potential outcomes comprising at least one definite outcome and at least one indefinite outcome;

evaluating the adjudication request and creating a primary determination using a processor and a memory by applying a first rule of the appropriate rule library to the adjudication request, using data objects from the adjudication request indicated by at least one data tag of the first rule;

applying a first subsequent rule of the at least one subsequent rules and all logically adjacent rules within the appropriate rule library until all logically adjacent rules have been exhausted and the primary determination is an indefinite outcome or until the applying of a final rule returns an outcome that becomes the primary determination;

sending an adjudication result to the second client through the network interface comprising at least the primary determination;

wherein the external value is obtained outside of the adjudication request.

13. The method of claim 12, further comprising:
receiving a new rule through the network interface from a first client; and
storing the new rule in one of the at least one rule library.

14. The method of claim 12, further comprising:
sending, for primary determinations having an indefinite outcome, an escalated request to a first client through the network interface, the escalated request comprising at least the adjudication request; and
receiving a secondary determination from the first client, the secondary determination indicating the result of an evaluation of the escalated request performed by a first agent;
wherein the adjudication result is sent to the second client in response to one of the primary determination having a definite outcome and the receipt of a secondary determination, the adjudication result comprising one of the primary determination and the secondary determination.

15. The method of claim 14, wherein the adjudication result sent in response to the receipt of a secondary determination comprises the primary determination and the secondary determination.

16. The method of claim 14, further comprising:
creating a first probationary rule in response to the receipt of the secondary determination, the first probationary rule functioning as an exception to a target rule, wherein the first data tag of the first probationary rule is the same as the first data tag of the target rule, the result of the first probationary rule is equal to the secondary determination, and wherein at least one of the comparator and the comparison value of the first probationary rule deviates from what is defined in the target rule to create an exception that, when applied to the adjudication request before the application of the target rule, the result is the same as the secondary determination;
storing the first probationary rule within a storage, the first probationary rule further comprising a success rate;
adding to the target rule a reference pointing to the first probationary rule within the storage;
applying the first probationary rule to another adjudication request resulting in the application of the target rule and the sending of another escalated request;
comparing the secondary determination received in response to the another escalated request with the result of the application of the first probationary rule to the another adjudication request, and updating the success rate of the first probationary rule;
refining the first probationary rule by one of modifying at least one of the comparator and the comparison value of the first probationary rule and creating a second probationary rule as an exception to the first probationary rule, in response to the first probationary rule's failure to match the secondary determination received in response to the another escalated request; and
inserting the first probationary rule into the appropriate rule library in response to at least one of the receipt of a manual approval and the success rate of the first probationary rule surpassing a predefined threshold.

17. The method of claim 12,
wherein the adjudication request is a request for prior authorization and comprises patient information, policy information, and treatment information comprising a medical code;
wherein the first client is an insurance provider client;
wherein the second client is a healthcare provider client;
wherein the at least one definite outcome comprises an approval, a denial, and an indication that prior authorization is not required; and
wherein the at least one indefinite outcome comprises an indication that the request cannot be evaluated.

18. The method of claim 12, wherein each rule of the plurality of rules is in a human-readable format.

19. The method of claim 18, further comprising:
providing, through the network interface, an interface in which at least one rule library is formatted and through which the at least one rule library is made available to a user as a human readable resource.

20. The method of claim 18, wherein at least one of the first data tag and the second data tag of at least one rule in the appropriate rule library is associated with a derived data object missing from the adjudication request and defined by an expression comprising one or more operations performed on at least one data object of the adjudication request.

* * * * *